United States Patent
Sugi et al.

(10) Patent No.: US 6,815,548 B2
(45) Date of Patent: *Nov. 9, 2004

(54) PROCESS FOR PREPARING A PIPERIDINE DERIVATIVE

(75) Inventors: Kiyoshi Sugi, Osaka (JP); Nobushige Itaya, Osaka (JP); Tadashi Katsura, Osaka (JP); Masami Igi, Osaka (JP); Shigeya Yamazaki, Osaka (JP); Taro Ishibashi, Osaka (JP); Teiji Yamaoka, Osaka (JP); Yoshihiro Kawada, Osaka (JP); Yayoi Tagami, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/336,678

(22) Filed: Jan. 6, 2003

(65) Prior Publication Data

US 2003/0144519 A1 Jul. 31, 2003

Related U.S. Application Data

(62) Division of application No. 09/695,383, filed on Oct. 25, 2000, now Pat. No. 6,610,851, which is a division of application No. 09/306,411, filed on May 6, 1999, now abandoned, which is a division of application No. 08/871,948, filed on Jun. 10, 1997, now abandoned.

(30) Foreign Application Priority Data

| Jun. 13, 1996 | (JP) | ............................................. | 8-175893 |
| Oct. 15, 1996 | (JP) | ............................................. | 8-294585 |
| Oct. 29, 1996 | (JP) | ............................................. | 8-303838 |
| Nov. 20, 1996 | (JP) | ............................................. | 8-326177 |
| Feb. 18, 1997 | (JP) | ............................................. | 9-050980 |

(51) Int. Cl.$^7$ .......................................... C07D 405/12
(52) U.S. Cl. ...................... 546/197; 546/216; 546/221; 514/321
(58) Field of Search .......................... 514/321; 546/197, 546/216, 221

(56) References Cited

U.S. PATENT DOCUMENTS

| 3,912,743 A | 10/1975 | Christensen et al. | ........ 546/210 |
| 4,003,922 A | 1/1977 | Kavadias et al. | ........... 549/525 |

(List continued on next page.)

FOREIGN PATENT DOCUMENTS

| DE | 2404113 | 8/1974 |
| EP | 0190496 A2 | 8/1986 |
| EP | 190496 A2 | 8/1986 |
| EP | 0223334 A1 | 5/1987 |
| EP | 0223403 A2 | 5/1987 |
| EP | 0266574 A2 | 5/1988 |
| EP | 0 626 301 A1 | 11/1994 |
| EP | 0802185 A1 | 10/1997 |
| EP | 0810225 A1 | 12/1997 |
| EP | 0 990 655 A | 4/2000 |
| JP | 61 007238 A | 1/1986 |
| JP | 03 279375 A | 12/1991 |
| JP | 04 108773 A | 4/1992 |
| JP | 6316563 A | 11/1994 |
| WO | WO 9421609 A1 | 9/1994 |
| WO | WO 9525732 A1 | 9/1995 |
| WO | WO9624595 A1 | 8/1996 |
| WO | WO 9636636 A1 | 11/1996 |
| WO | 00/08017 A | 3/2000 |

OTHER PUBLICATIONS

Buxton et al., *Analytical Proceedings*, vol. 25, pp. 305–306 (1988).
Chemical Abstracts; 121:230462y (1994).
Montzka et al., *Journal of Organic Chemistry*, vol. 33, pp. 3393–3395 (1986).
Amat et al., *Tetrahedron: Asymmetry*, vol. 7, No. 6, pp. 1591–1594 (1996).

(List continued on next page.)

Primary Examiner—Celia Chang
(74) Attorney, Agent, or Firm—Birch, Stewart, Kolasch & Birch, LLP

(57) ABSTRACT

A piperidine derivative, which can be used as an intermediate for pharmaceuticals such as paroxetine useful as antidepressants, represented by the general formula (I):

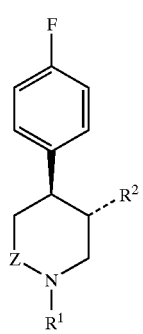

(I)

wherein $R^1$ is hydrogen atom, benzyloxycarbonyl group or tert-butoxycarbonyl group; $R^2$ is hydroxymethyl group, an alkylsulfonyloxymethyl group having an alkyl moiety of 1 to 2 carbon atoms, phenylsulfonyloxymethyl group which may have methyl group at the 4-position, (3,4-methylenedioxyphenyl)oxymethyl group, carboxyl group or —$CO_2R^7$ group in which $R^7$ is an alkyl group having 1 to 5 carbon atoms, and Z is methylene group or carbonyl group, with proviso that, (A) when $R^1$ is benzyloxycarbonyl group or tert-butoxycarbonyl group, then $R^2$ is hydroxymethyl group, an alkylsulfonyloxymethyl group having an alkyl moiety of 1 to 2 carbon atoms, phenylsulfonyloxymethyl group which may have methyl group at the 4-position or (3,4-methylenedioxyphenyl)oxymethyl group, and Z is methylene group; or (B) when $R^1$ is hydrogen atom and Z is carbonyl group, then $R^2$ is carboxyl group or —$CO_2R^7$ group ($R^7$ is as defined above); or (C) when $R^1$ is hydrogen atom and Z is methylene group, then $R^2$ is hydroxymethyl group.

4 Claims, No Drawings

U.S. PATENT DOCUMENTS

| | | | |
|---|---|---|---|
| 4,007,196 A | 2/1977 | Christensen et al. | 546/210 |
| 4,062,839 A | 12/1977 | Sifniades et al. | 540/485 |
| 4,721,723 A | 1/1988 | Barnes et al. | 514/321 |
| 4,861,893 A | 8/1989 | Borrett | 546/210 |
| 4,902,801 A | 2/1990 | Faruk et al. | 546/220 |
| 5,039,803 A | 8/1991 | Smith et al. | 546/185 |
| 5,258,517 A | 11/1993 | Zepp et al. | 546/240 |
| 5,856,493 A | 1/1999 | Ward et al. | 546/197 |
| 5,872,132 A * | 2/1999 | Ward et al. | 514/321 |
| 6,197,960 B1 | 3/2001 | Wang et al. | 546/220 |
| 6,433,179 B1 | 8/2002 | Wang et al. | 546/197 |
| 6,444,822 B1 | 9/2002 | De Ferra et al. | 546/197 |
| 6,476,228 B1 | 11/2002 | Wang et al. | 546/235 |

OTHER PUBLICATIONS

Greene TW & Wuts PGM, *Protective Groups in Organic Synthesis, Second Edition*, John Wiley & Sons, Inc., pp. 1 335–337, 327–329 (1982).

Willcocks et al., *J. Labelled Compd. Radiopharm.*, vol. 33, No. 8, pp. 783–794 (Mar. 1993).

Engelstroft et al., *ACTA Chemica Scandinavica*, vol. 50, No. 2, pp. 164–169 (Feb. 1996).

Mathis et al., *J. Pharm. Pharmacol.*, vol. 44, No. 10, pp. 801–805 (1992).

Herdeis et al., *Tetrahedron: Asymetry*, vol. 7, No. 3 pp. 867–884 (Mar. 1996).

Spanish Patent Application No. 9600369 filed Feb. 16, 1996.

Spanish Patent Application No. 9600818 filed Apr. 10, 1996.

Chemical Abstracts, 94:14772 (1980).

Hartter et al., *Ther. Drug Monit.*, vol. 16, No. 4, pp. 400–406 (1994).

Strijewski et al., *Life Science*, vol. 47, No. 14, pp. 1213–1219 (1990).

Willcocks et al., *J. Labelled Compd. Radiopharm.*, vol. 33, No. 8, pp. 777–781 (Mar. 1993).

*Chemical Abstracts*, 114:6300S (1991).

Plati et al., *J. Org. Chem*, vol. 22, pp. 261–265 (Mar. 1957).

Koblsch, C.F., *JACS*, vol. 65, pp. 2459–2460 (1943).

Moos et al., *J. Org. Chem.*, vol. 46, pp. 5064–5074 (1981).

Buxton et al., *International Journal of Pharmaceutics*, vol. 42, pp. 135–143 (1988).

Jacques J. et al., "Enantiomers, Racemates and Resolutions"; pp. 259–261 and 387–388; (1991), XP002030514.

* cited by examiner

PROCESS FOR PREPARING A PIPERIDINE DERIVATIVE

This application is a divisional of application Ser. No. 09/695,383, filed on Oct. 25, 2000, now U.S. Pat. No. 6,610,851 which is a Divisional of Ser. No. 09/306,411 filed May 6, 1999, now abandoned, which is a Divisional of Ser. No. 08/871,948 filed Jun. 10, 1997, now abandoned, the entire contents of which are hereby incorporated by reference and for which priority is claimed under 35 U.S.C. §120; and this application claims priority of Application No. 8-175893, 8-294585, 8-303838, 8-326177 and 9-50980 filed in Japan on Jun. 13, 1996, Oct. 15, 1996, Oct. 29, 1996, Nov. 20, 1996, and Feb. 18, 1997, respectively under 35 U.S.C. §119.

BACKGROUND OF THE INVENTION

1. Field of the Invention

The present invention relates to a piperidine derivative and a process for preparing the same More particularly, the present invention relates to a piperidine derivative useful as an intermediate for pharmaceuticals such as paroxetine and the like which are useful, for example, as an antidepressant.

2. Discussion of the Related Art

In general, paroxetine useful as an antidepressant is prepared by the processes described, for example, in Japanese Unexamined Patent Publication No. 7-138228 and Japanese Examined Patent Publication No. 59-46216.

However, these processes have the drawback that, upon deprotection of N-methyl group, complicated procedures such as hydrolysis after the transformation of N-methyl group to carbamate group are required.

In addition, there is disclosed a process for preparing paroxetine using an amidomalonic acid ester derivative as a starting material in, for example, Japanese Unexamined Patent Publication No. 7-138228. However, the amidomalonic acid ester derivative is not in general commercially available. Therefore, there necessitates troublesome procedures such that the amidomalonic acid ester derivative should be previously prepared before using.

An object of the present invention is to provide a compound useful as an intermediate for preparing paroxetine and a process for simply and industrially preparing the compound.

These and other objects of the present invention will be apparent from the following description.

SUMMARY OF THE INVENTION

Specifically, the present invention is concerned with the following:

(1) A piperidine derivative represented by the general formula (I):

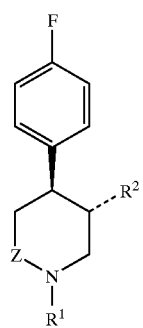

(I)

wherein $R^1$ is hydrogen atom, benzyloxycarbonyl group or tert-butoxycarbonyl group; $R^2$ is hydroxymethyl group, an alkylsulfonyloxymethyl group having an alkyl moiety of 1 to 2 carbon atoms, phenylsulfonyloxymethyl group which may have methyl group at the 4-position, (3,4-methylenedioxyphenyl)oxymethyl group, carboxyl group or —$CO_2R^7$ group in which $R^7$ is an alkyl group having 1 to 5 carbon atoms, and Z is methylene group or carbonyl group, with proviso that, (A) when $R^1$ is benzyloxycarbonyl group or tert-butoxycarbonyl group, then $R^2$ is hydroxymethyl group, an alkylsulfonyloxymethyl group having an alkyl moiety of 1 to 2 carbon atoms, phenylsulfonyloxymethyl group which may have methyl group at the 4-position or (3,4-methylenedioxyphenyl)oxymethyl group, and Z is methylene group; or (B) when $R^1$ is hydrogen atom and Z is carbonyl group, then $R^2$ is carboxyl group or —$CO_2R^7$ group ($R^7$ is as defined above); or (C) when $R^1$ is hydrogen atom and Z is methylene group, then $R^2$ is hydroxymethyl group;

(2) The piperidine derivative described in the above item (1), wherein the piperidine derivative is at least one member selected from (3S,4R)-trans-1-benzyloxycarbonyl-4-(4-fluorophenyl)-3-[(3,4-methylenedioxyphenyl)-oxymethyl]piperidine, (3SR,4RS)-trans-1-benzyloxy-4-(4-fluorophenyl)-3-[(3,4-methylenedioxyphenyl)oxymethyl]-piperidine, (3S,4R)-trans-1-tert-butoxycarbonyl-4-(4-fluorophenyl)-3-[(3,4-methylenedioxyphenyl)oxymethyl]-piperidine, (3SR,4RS)-trans-1-tert-butoxycarbonyl-4-(4-fluorophenyl)-3-[(3,4-methylenedioxyphenyl)oxymethyl]-piperidine, (3S,4R)-trans-1-benzyloxycarbonyl-4-(4-fluorophenyl)-3-methylsulfonyloxymethylpiperidine, (3SR,4RS)-trans-1-benzyloxycarbonyl-4-(4-fluorophenyl)-3-methylsulfonyloxymethylpiperidine, (3S,4R)-trans-1-tert-butoxycarbonyl-4-(4-fluorophenyl)-3-methylsulfonyloxymethylpiperidine, (3SR,4RS)-trans-1-tert-butoxycarbonyl-4-(4-fluorophenyl)-3-methylsulfonyloxymethylpiperidine, (3S,4R)-trans-1-benzyloxycarbonyl-4-(4-fluorophenyl)-3-ethylsulfonyloxymethylpiperidine, (3SR,4RS)-trans-1-benzyloxycarbonyl-4-(4-fluorophenyl)-3-ethylsulfonyloxymethylpiperidine, (3S,4R)-trans-1-tert-butoxycarbonyl-4-(4-fluorophenyl)-3-ethylsulfonyloxymethylpiperidine, (3SR,4RS)-trans-1-tert-butoxycarbonyl-4-(4-fluorophenyl)-3-ethylsulfonyloxymethylpiperidine, (3S,4R)-trans-1-benzyloxycarbonyl-4-(4-fluorophenyl)-3-phenylsulfonyloxymethylpiperidine, (3SR,4RS)-trans-1-benzyloxycarbonyl-4-(4-fluorophenyl)-3-phenylsulfonyloxymethylpiperidine, (3S,4R)-trans-1-tert-butoxycarbonyl-4-(4-fluorophenyl)-3-phenylsulfonyloxymethylpiperidine, (3SR,4RS)-trans-1-tert-butoxycarbonyl-4-(4-fluorophenyl)-3-phenylsulfonyloxymethylpiperidine, (3S,4R)-trans-1-benzyloxycarbonyl-4-(4-fluorophenyl)-3-(4-methylphenyl)sulfonyloxymethylpiperidine, (3SR,4RS)-trans-1-benzyloxycarbonyl-4-(4-fluorophenyl)-3-(4-methylphenyl)sulfonyloxymethylpiperidine, (3S,4R)-trans-1-tert-butoxycarbonyl-4-(4-fluorophenyl)-3-(4-methylphenyl)sulfonyloxymethylpiperidine, (3SR,4RS)-trans-1-tert-butoxycarbonyl-4-(4-fluorophenyl)-3-(4-methylphenyl)sulfonyloxymethylpiperidine, (3S,4R)-trans-1-benzyloxycarbonyl-4-(4-fluorophenyl)-3-hydroxymethylpiperidine, (3SR,4RS)-trans-1-benzyloxycarbonyl-4-(4-fluorophenyl)-3-hydroxymethylpiperidine, (3S,4R)-trans-1-tert-butoxycarbonyl-4-(4-fluorophenyl)

-3-hydroxymethylpiperidine, (3SR,4RS)-trans-1-tert-butoxycarbonyl-4-(4-fluorophenyl)-3-hydroxymethylpiperidine, (3S,4R)-trans-4-(4-fluorophenyl)-3-hydroxymethylpiperidine, (4R,5S)-trans-5-carboxy-4-(4-fluorophenyl)piperidin-2-one, and (4RS,5SR)-trans-5-carboxy-4-(4-fluorophenyl)piperidin-2-one;

(3) The piperidine derivative described in the above item (1), wherein $R^1$ is tert-butoxycarbonyl group or benzyloxycarbonyl group, $R^2$ is a group represented by the formula:

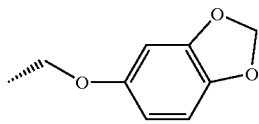

and Z is methylene group in the general formula (I);

(4) A method for preparing a piperidine derivative represented by the general formula (VII);

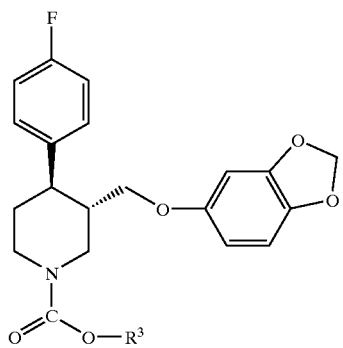

(VII)

wherein $R^3$ is benzyl group or tert-butyl group, comprising the steps of:

reacting (3S,4R)-trans-4-(4-fluorophenyl)-3-hydroxymethylpiperidine represented by the formula (II):

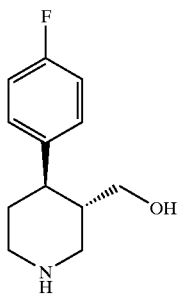

(II)

with a protecting reagent represented by the general formula (III):

(III)

wherein $R^3$ is as defined above; and Y is a chlorine atom or tert-butoxycarbonyloxy group, with proviso that (A) when $R^3$ is benzyl group, then Y is a chlorine atom, (B) when $R^3$ is tert-butyl group, then Y is tert-butoxycarbonyloxy group, to give a carbamate compound represented by the general formula (IV):

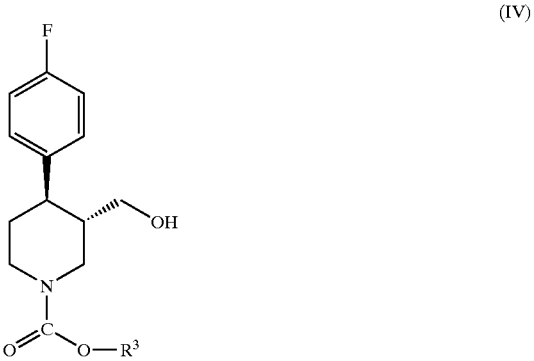

(IV)

wherein $R^3$ is as defined above;

reacting the carbamate compound with a sulfonic acid chloride represented by the general formula (V):

(V)

wherein $R^4$ is an alkyl group having 1 to 2 carbon atoms or a phenyl group which may have methyl group at the 4-position, to give a sulfonic acid ester represented by the general formula (VI):

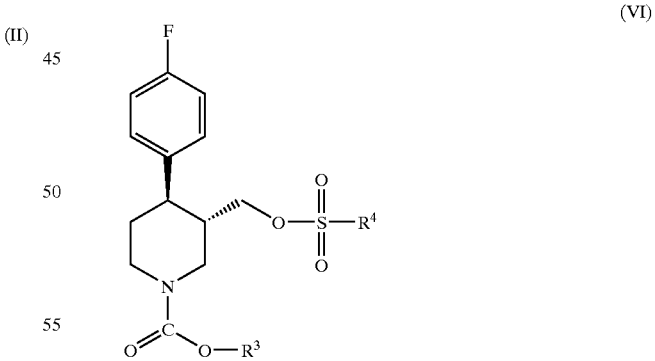

(VI)

wherein $R^3$ and $R^4$ are as defined above;

reacting the sulfonic acid ester with 3,4-methylenedioxyphenol under basic conditions;

(5) A method for preparing (3S,4R)-trans-4-(4-fluorophenyl)-3-hydroxymethylpiperidine represented by the formula (II):

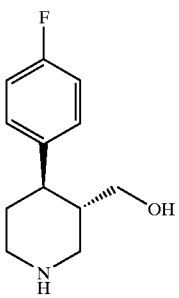

(II)

comprising the steps of:

optically resolving (4RS,5SR)-trans-5-carboxy-4-(4-fluorophenyl)piperidin-2-one, to give (4R,5S)-trans-5-carboxy-4-(4-fluorophenyl)piperidin-2-one represented by the formula (VIII):

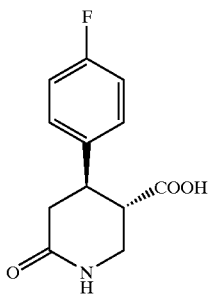

(VIII)

and reducing the (4R,5S)-trans-5-carboxy-4-(4-fluorophenyl)piperidine with a metal hydride compound;

(6) A method for preparing (3S,4R)-trans-4-(4-fluorophenyl)-3-hydroxymethylpiperidine represented by the formula (II):

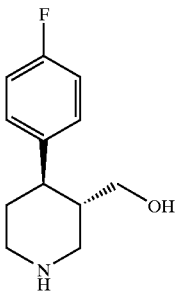

(II)

comprising the step of optically resolving (3SR,4RS)-trans-4-(4-fluorophenyl)-3-hydroxymethylpiperidine;

(7) A method for preparing (3S,4R)-trans-4-(4-fluorophenyl)-3-hydroxymethylpiperidine represented by the formula (II):

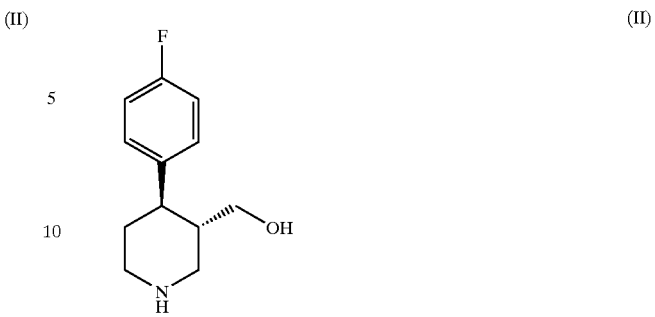

(II)

comprising the steps of:

transforming (±)-cis,trans-4-(4-fluorophenyl)-5-alkyloxycarbonylpiperidin-2-one represented by the general formula (IX):

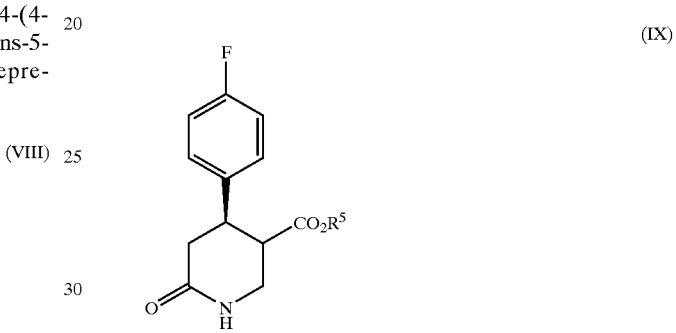

(IX)

wherein $R^5$ is an alkyl group having 1 to 4 carbon atoms; in the presence of a base, to give (4RS,5SR)-trans-4-(4-fluorophenyl)-5-alkyloxycarbonylpiperidin-2-one;

reducing the (4RS,5SR)-trans-4-(4-fluorophenyl)-5-alkoxycarbonylpiperidin-2-one with a metal hydride compound, to give (3SR,4RS)-trans-4-(4-fluorophenyl)-3-hydroxymethylpiperidine; and optically resolving the (3SR,4RS)-trans-4-(4-fluorophenyl)-3-hydroxymethylpiperidine;

(8) A method for preparing (3S,4R)-trans-4-(4-fluorophenyl)-3-[(3,4-methylenedioxyphenyl)oxymethyl]-piperidine comprising the step of catalytically reducing (3S,4R)-trans-1-benzyloxycarbonyl-4-(4-fluorophenyl)-3-[(3,4-methylenedioxyphenyl)oxymethyl]piperidine, to deprotect the benzyloxycarbonyl group;

(9) A method for preparing a hydrochloride of (3S,4R)-trans-4-(4-fluorophenyl)-3-[(3,4-methylenedioxyphenyl)-oxymethyl]piperidine comprising the steps of:

catalytically reducing (3S,4R)-trans-1-benzyloxycarbonyl-4-(4-fluorophenyl)-3-[(3,4-methylenedioxyphenyl)oxymethyl]piperidine, to deprotect the benzyloxycarbonyl group, to give (3S,4R)-trans-4-(4-fluorophenyl)-3-[(3,4-methylenedioxyphenyl)oxymethyl]-piperidine; and treating the (3S,4R)-trans-4-(4-fluorophenyl)-3-[(3,4-methylenedioxyphenyl)oxymethyl]piperidine with hydrogen chloride;

(10) The method described in the above item (9), wherein the (3S,4R)-trans-4-(4-fluorophenyl)-3-[(3,4-methylenedioxyphenyl)oxymethyl]piperidine is treated with hydrogen chloride in isopropanol;

(11) A method for preparing a hydrochloride of (3S,4R)-trans-4-(4-fluorophenyl)-3-[(3,4-methylenedioxyphenyl)-oxymethyl]piperidine comprising the step of treating (3S,4R)-trans-1-tert-butoxycarbonyl-4-(4-fluorophenyl)-3-[(3,4-methylenedioxyphenyl)oxymethyl]piperidine with hydrogen chloride;

(12) The method described in the above item (11), wherein the (3S,4R)-trans-4-(4-fluorophenyl)-3-[(3,4-methylenedioxyphenyl)oxymethyl]piperidine is treated with hydrogen chloride in isopropanol;

(13) A method for preparing a hydrochloride of (3S,4R)-trans-4-(4-fluorophenyl)-3-[(3,4-methylenedioxyphenyl)oxymethyl]piperidine containing isopropanol, comprising the step of treating the isopropanol solution of a hydrochloride of (3S,4R)-trans-4-(4-fluorophenyl)-3-[(3,4-methylenedioxyphenyl)-oxymethyl]piperidine prepared by a method described in the above item (10) or item (12) with active carbon, to remove impurities; and

(14) A method for preparing an anhydrous hydrochloride of (3S,4R)-trans-4-(4-fluorophenyl)-3-[(3,4-methylenedioxyphenyl)oxymethyl]piperidine having an isopropanol content of 0.1 to 5% by weight, comprising the steps of:

allowing precipitation of crystals of a hydrochloride of (3S,4R)-trans-4-(4-fluorophenyl)-3-[(3,4-methylenedioxyphenyl)oxymethyl]piperidine from the isopropanol solution of the hydrochloride of (3S,4R)-trans-4-(4-fluorophenyl)-3-[(3,4-methylenedioxyphenyl)-oxymethyl]piperidine prepared by a method described in the above item (10), item (12), or item (13); and drying the crystals under a reduced pressure at a temperature of from 80° to 110° C.

DETAILED DESCRIPTION OF THE INVENTION

As described above, the piperidine derivative of the present invention is a compound represented by the general formula (I):

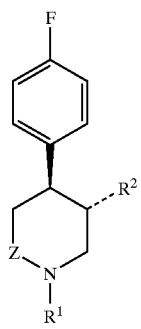

(I)

wherein $R^1$ is hydrogen atom, benzyloxycarbonyl group or tert-butoxycarbonyl group; $R^2$ is hydroxymethyl group, an alkylsulfonyloxymethyl group having an alkyl moiety of 1 to 2 carbon atoms, phenylsulfonyloxymethyl group which may have methyl group at the 4-position, (3,4-methylenedioxyphenyl)oxymethyl group, carboxyl group or —$CO_2R^7$ group in which $R^7$ is an alkyl group having 1 to 5 carbon atoms, and Z is methylene group or carbonyl group, with proviso that, (A) when $R^1$ is benzyloxycarbonyl group or tert-butoxycarbonyl group, then $R^2$ is hydroxymethyl group, an alkylsulfonyloxymethyl group having an alkyl moiety of 1 to 2 carbon atoms, phenylsulfonyloxymethyl group which may have methyl group at the 4-position or (3,4-methylenedioxyphenyl)oxymethyl group, and Z is methylene group;

(B) when $R^1$ is hydrogen atom and Z is carbonyl group, then $R^2$ is carboxyl group or —$CO_2R^7$ group ($R^7$ is as defined above); and (C) when $R^1$ is hydrogen atom and Z is methylene group, then $R^2$ is hydroxymethyl group.

In the general formula (I), $R^1$ is hydrogen atom, benzyloxycarbonyl group or tert-butoxycarbonyl group. $R^2$ is hydroxymethyl group, an alkylsulfonyloxymethyl group having an alkyl moiety of 1 to 2 carbon atoms, phenylsulfonyloxymethyl group which may have methyl group at the 4-position, (3,4-methylenedioxyphenyl)oxymethyl group, carboxyl group or —$CO_2R^7$ group in which $R^7$ is as defined above. Z is methylene group or carbonyl group.

(A) When $R^1$ is benzyloxycarbonyl group or tert-butoxycarbonyl group, then $R^2$ is hydroxymethyl group, an alkylsulfonyloxymethyl group having an alkyl moiety of 1 to 2 carbon atoms, phenylsulfonyloxymethyl group which may have methyl group at the 4-position or (3,4-methylenedioxyphenyl)oxymethyl group, and Z is methylene group.

(B) When $R^1$ is hydrogen atom and Z is carbonyl group, then $R^2$ is carboxyl group or —$CO_2R^7$ group ($R^7$ is as defined above).

(C) When $R^1$ is hydrogen atom and Z is methylene group, $R^2$ is hydroxymethyl group.

In the general formula (I), (A) when $R^1$ is benzyloxycarbonyl group or tert-butoxycarbonyl group, then $R^2$ is hydroxymethyl group, an alkylsulfonyloxymethyl group having an alkyl moiety of 1 to 2 carbon atoms, phenylsulfonyloxymethyl group which may have methyl group at the 4-position or (3,4-methylenedioxyphenyl)oxymethyl group, and Z is methylene group; and (C) when $R^1$ is hydrogen atom and Z is methylene group, then $R^2$ is hydroxymethyl group, there can be cited as the specific examples of the piperidine derivative represented by the general formula (I), for instance, (3S,4R)-trans-4-(4-fluorophenyl)-3-hydroxymethylpiperidine, (3S,4R)-trans-1-benzyloxycarbonyl-4-(4-fluorophenyl)-3-hydroxymethylpiperidine, (3S,4R)-trans-1-benzyloxycarbonyl-4-(4-fluorophenyl)-3-methylsulfonyloxymethylpiperidine, (3S,4R)-trans-1-benzyloxycarbonyl-4-(4-fluorophenyl)-3-ethylsulfonyloxymethylpiperidine, (3S,4R)-trans-1-benzyloxycarbonyl-4-(4-fluorophenyl)-3-phenylsulfonyloxymethylpiperidine, (3S,4R)-trans-1-benzyloxycarbonyl-4-(4-fluorophenyl)-3-(p-toluylsulfonyloxymethyl)piperidine, (3S,4R)-trans-1-benzyloxycarbonyl-4-(4-fluorophenyl)-3-[(3,4-methylenedioxyphenyl)oxymethyl]piperidine, (3SR,4RS)-trans-4-(4-fluorophenyl)-3-hydroxymethylpiperidine, (3SR,4RS)-trans-1-benzyloxycarbonyl-4-(4-fluorophenyl)-3-hydroxymethylpiperidine, (3SR,4RS)-trans-1-benzyloxycarbonyl-4-(4-fluorophenyl)-3-methylsulfonyloxymethylpiperidine, (3SR,4RS)-trans-1-benzyloxycarbonyl-4-(4-fluorophenyl)-3-ethylsulfonyloxymethylpiperidine, (3SR,4RS)-trans-1-benzyloxycarbonyl-4-(4-fluorophenyl)-3-phenylsulfonyloxymethylpiperidine, (3SR,4RS)- trans-1-benzyloxycarbonyl-4-(4-fluorophenyl)-3-(4-methylphenyl)sulfonyloxymethylpiperidine, (3SR, 4RS)-trans-1-benzyloxycarbonyl-4-(4-fluorophenyl)-3-[(3,4-methylenedioxyphenyl)oxymethyl]piperidine, (3S,4R)-trans-1-tert-butoxycarbonyl-4-(4-fluorophenyl)-3-[(3,4-methylenedioxyphenyl)oxymethyl]piperidine, (3SR, 4RS)-trans-1-tert-butoxycarbonyl-4-(4-fluorophenyl)-3-[(3,4-methylenedioxyphenyl)oxymethyl]piperidine, (3S,4R)-trans-1-tert-butoxycarbonyl-4-(4-fluorophenyl)-3-methylsulfonyloxymethylpiperidine, (3SR,4RS)-trans-1-tert-butoxycarbonyl-4-(4-fluorophenyl)-3-methylsulfonyloxymethylpiperidine, (3S,4R)-trans-1-tert-butoxycarbonyl-4-(4-fluorophenyl)-3-ethylsulfonyloxymethylpiperidine, (3SR,4RS)-trans-1-tert-butoxycarbonyl-4-(4-fluorophenyl)-3-ethylsulfonyloxymethylpiperidine, (3S,4R)-trans-1-tert-butoxycarbonyl-4-(4-fluorophenyl)-3-phenylsulfonyloxymethylpiperidine, (3SR,4RS)-trans-1-tert-butoxycarbonyl-4-(4-fluorophenyl)-3-phenylsulfonyloxymethylpiperidine, (3S,4R)-trans-1-tert-butoxycarbonyl-4-(4-fluorophenyl)-3-(4-methylphenyl)sulfonyloxymethylpiperidine, (3SR, 4RS)-trans-1-tert-butoxycarbonyl-4-(4-fluorophenyl)-3-(4-methylphenyl)sulfonyloxymethylpiperidine, (3S,4R)-trans-1-tert-butoxycarbonyl-4-(4-fluorophenyl)-3-hydroxymethylpiperidine, and (3SR,4RS)-trans-1-tert-butoxycarbonyl-4-(4-fluorophenyl)-3-hydroxymethylpiperidine.

In the general formula (I), when $R^1$ is hydrogen atom and Z is carbonyl group, and $R^2$ is carboxyl group or $-CO_2R^7$ group, in which $R^7$ is as defined above, examples of the piperidine derivatives represented by the general formula (I) include (±)-trans-4-(4-fluorophenyl)-5-methoxycarbonylpiperidin-2-one, (±)-trans-4-(4-fluorophenyl)-5-ethoxycarbonylpiperidin-2-one, (±)-trans-4-(4-fluorophenyl)-5-propoxycarbonylpiperidin-2-one, (±)-trans-4-(4-fluorophenyl)-5-isopropoxycarbonylpiperidin-2-one, (±)-trans-4-(4-fluorophenyl)-5-butoxycarbonylpiperidin-2-one, (±)-trans-5-carboxy-4-(4-fluorophenyl)piperidin-2-one, (±)-cis-4-(4-fluorophenyl)-5-methoxycarbonylpiperidin-2-one, (±)-cis-4-(4-fluorophenyl)-5-ethoxycarbonylpiperidin-2-one, (±)-cis-4-(4-fluorophenyl)-5-propoxycarbonylpiperidin-2-one, (±)-cis-4-(4-fluorophenyl)-5-isopropoxycarbonylpiperidin-2-one, (±)-cis-4-(4-fluorophenyl)-5-butoxycarbonylpiperidin-2-one, and (±)-cis-5-carboxy-4-(4-fluorophenyl)piperidin-2-one.

Among the above piperidine derivatives, there can be particularly preferably used in the present invention, at least one member selected from (3S,4R)-trans-1-benzyloxycarbonyl-4-(4-fluorophenyl)-3-[(3,4-methylenedioxyphenyl)oxymethyl]piperidine, (3SR,4RS)-trans-1-benzyloxycarbonyl-4-(4-fluorophenyl)-3-[(3,4-methylenedioxyphenyl)oxymethyl]piperidine, (3S,4R)-trans-1-tert-butoxycarbonyl-4-(4-fluorophenyl)-3-[(3,4-methylenedioxyphenyl)oxymethyl]-piperidine, (3SR, 4RS)-trans-1-tert-butoxycarbonyl-4-(4-fluorophenyl)-3-[(3,4-methylenedioxyphenyl)oxymethyl]-piperidine, (3S,4R)-trans-1-benzyloxycarbonyl-4-(4-fluorophenyl)-3-methylsulfonyloxymethylpiperidine, (3SR,4RS)-trans-1-benzyloxycarbonyl-4- (4-fluorophenyl)-3-methylsulfonyloxymethylpiperidine, (3S, 4R)-trans-1-tert-butoxycarbonyl-4-(4-fluorophenyl)-3-methylsulfonyloxymethylpiperidine, (3SR,4RS)-trans-1-tert-butoxycarbonyl-4-(4-fluorophenyl)-3-methylsulfonyloxymethylpiperidine, (3S, 4R)-trans-1-benzyloxycarbonyl-4-(4-fluorophenyl)-3-ethylsulfonyloxymethylpiperidine, (3SR,4RS)-trans-1-benzyloxycarbonyl-4-(4-fluorophenyl)-3-ethylsulfonyloxymethylpiperidine, (3SR,4RS)-trans-1-tert-butoxycarbonyl-4-(4-fluorophenyl)-3-ethylsulfonyloxymethylpiperidine, (3S,4R)-trans-1-benzyloxycarbonyl-4-(4-fluorophenyl)-3-phenylsulfonyloxymethylpiperidine, (3SR,4RS)-trans-1-benzyloxycarbonyl-4-(4-fluorophenyl)-3-phenylsulfonyloxymethylpiperidine, (3S,4R)-trans-1-tert-butoxycarbonyl-4-(4-fluorophenyl)-3-phenylsulfonyloxymethylpiperidine, (3SR,4RS)-trans-1-tert-butoxycarbonyl-4-(4-fluorophenyl)-3-phenylsulfonyloxymethylpiperidine, (3S,4R)-trans-1-benzyloxycarbonyl-4-(4-fluorophenyl)-3-(4-methylphenyl)sulfonyloxymethylpiperidine, (3SR,4RS)-trans-1-benzyloxycarbonyl-4-(4-fluorophenyl)-3-(4-methylphenyl)sulfonyloxymethylpiperidine, (3S,4R)-trans-1-tert-butoxycarbonyl-4-(4-fluorophenyl)-3-(4-methylphenyl)sulfonyloxymethylpiperidine, (3SR,4RS)-trans-1-tert-butoxycarbonyl-4-(4-fluorophenyl)-3-(4-methylphenyl)sulfonyloxymethylpiperidine, (3S,4R)-trans-1-benzyloxycarbonyl-4-(4-fluorophenyl)-3-hydroxymethylpiperidine, (3SR,4RS)-trans-1-benzyloxycarbonyl-4-(4-fluorophenyl)-3-hydroxymethylpiperidine, (3S,4R)-trans-1-tert-butoxycarbonyl-4-(4-fluorophenyl)-3-hydroxymethylpiperidine, (3SR,4RS)-trans-1-tert-butoxycarbonyl-4-(4-fluorophenyl)-3-hydroxymethylpiperidine, (3S,4R)-trans-4-(4-fluorophenyl)-3-hydroxymethylpiperidine, (4R,5S)-trans-5-carboxy-4-(4-fluorophenyl)piperidin-2-one, and (4RS,5SR)-trans-5-carboxy-4-(4-fluorophenyl)piperidin-2-one.

As the starting material for the piperidine derivative represented by the general formula (I), 4-fluorobenzaldehyde can be used.

The above 4-fluorobenzaldehyde is reacted with an acetic acid ester represented by the general formula:

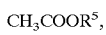

wherein $R^5$ is an alkyl group having 1 to 4 carbon atoms to give a 4-fluorocinnamic acid ester. A cyanoacetic acid ester represented by the general formula:

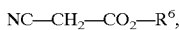

wherein $R^6$ is an alkyl group having 1 to 4 carbon atoms is reacted with the resulting 4-fluorocinnamic acid ester to give a glutaric acid ester derivative represented by the general formula (X):

(X)

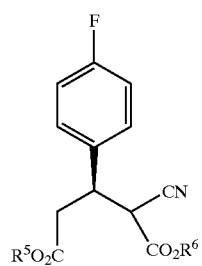

wherein $R^5$ and $R^6$ are as defined above. Then, the resulting glutaric acid ester derivative can be reduced to give (±)-cis, trans-4-(4-fluorophenyl)-5-alkyloxycarbonylpiperidin-2-one represented by the general formula (IX):

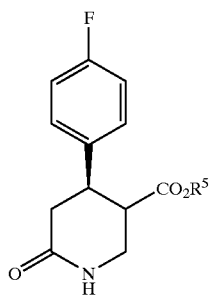

(IX)

wherein $R^5$ is as defined above.

The reduction is preferably catalytic hydrogenation, and the reaction conditions are not limited to specified ones. When the catalytic hydrogenation is performed, for example, a conventional catalytic hydrogenation conditions can be employed where cyano group of the glutaric acid ester derivative represented by the general formula (X) is catalytically hydrogenated to aminomethyl group. In this case, as the catalyst, for example, Raney cobalt, Raney nickel, palladium-carbon, platinum-carbon and the like can be used. As a solvent, there can be cited, for instance, hydrocarbon solvents such as toluene, ester solvents such as ethyl acetate, ether solvents such as tetrahydrofuran (THF), alcohol solvents such as methanol, and a mixture thereof. The reaction temperature can be usually within a range of room temperature to 150° C., and the hydrogen pressure can be, for example, within a range of 0.5 to 150 kgf/cm². Upon reaction, starting materials containing the compound represented by the general formula (X) can be introduced in the reaction vessel at a time, or the compound represented by the general formula (X) can be added to the reaction system under pressure.

The compound (±)-cis, trans-4-(4-fluorophenyl)-5-alkyloxycarbonylpiperidin-2-one represented by the general formula (IX) includes a cis-isomer and a trans-isomer as main components. In order to obtain the trans-isomer and the cis-isomer from the mixture separately thereof, there can be employed a usual method for the separation of compounds, such as utilizing the solubility difference in a solvent, and a conventional column separation for organic compounds. The cis-isomer can be converted into the trans-isomer in the presence of a base. Also, the cis-isomer can be converted into the trans-isomer in the form of an acid, for example, by alkaline hydrolysis.

When the above-mentioned isomerization of the (±)-cis, trans esters is carried out, for example, by using a sodium alkoxide as a catalyst to obtain crystals, the trans-isomer can be preferentially obtained in the form of an ester.

Also, when (±)-cis, trans-esters are heated to reflux using sodium hydroxide in an alcohol or in water, the cis-ester is presumably first transformed into the trans-ester and hydrolyzed to give a trans-acid.

The (±)-cis,trans-4-(4-fluorophenyl)-5-alkoxycarbonylpiperidin-2-one represented by the general formula (IX) can be converted into an optically active trans-carboxylic acid or its ester by transforming the above compound into a trans-carboxylic acid ester in the same manner as the above and hydrolyzing its ester portion using, for example, an enzyme, or by transforming the above compound into a trans-carboxylic acid and asymmetrically esterifying its carboxylic acid portion using an enzyme.

Also, the above racemic trans-carboxylic acid can be resolved into an optically active trans-carboxylic acid by a usual method for preparing a diastereomer derivative, for example, by a method comprising preparing a salt of the above trans-carboxylic acid and an optically active amine, and separating the salt therefrom as crystals.

More specifically, the optical resolution of (±)-trans-carboxylic acid, that is, (4RS,5SR)-trans-5-carboxy-4-(4-fluorophenyl)piperidin-2-one, can be carried out usually in a solvent in the presence of an optically active amine.

Representative examples of the optically active amines include compounds disclosed, for example, in Japanese Unexamined Patent Publication No. 6-116214. More particularly, there can be cited, for instance, R-(+)-N-(4-hydroxyphenylmethyl)phenylmethylamine, and the like.

It is desired that the amount of the optically active amine to be used is 0.5 to 1.2 moles, preferably 0.6 to 1.1 moles per 1 mole of (4RS,5SR)-trans-5-carboxy-4-(4-fluorophenyl)piperidin-2-one.

Examples of the solvents include alcohols such as methanol, ethanol, esters such as ethyl acetate, and the like. Those solvents can be used alone or in admixture thereof. If necessary, those solvents can be used in admixture with water.

The (4RS,5SR)-trans-5-carboxy-4-(4-fluorophenyl) piperidin-2-one and the optically active amine can be dissolved in the solvent, mixed and allowed to stand or stirred to optically resolve the (4RS,5SR)-trans-5-carboxy-4-(4-fluorophenyl)piperidin-2-one.

At this stage, it is desired that the temperature of the mixture is usually −10° to 120° C., preferably 10° to 90° C.

After the completion of the optical resolution, the precipitated crystals of the salts are filtered and the resulting crystals are degraded under acidic or alkaline conditions.

When the resulting crystals of the salts are degraded under alkaline conditions, the crystals are treated with alkaline such as sodium hydroxide or the like in the presence of water, and optically active amine is extracted from its aqueous layer with an organic solvent. Thereafter, the alkaline aqueous solution is made acidic to give crystals of (4R,5S)-trans-5-carboxy-4-(4-fluorophenyl)piperidin-2-one.

Also, when the resulting crystals of the salts are degraded under acidic conditions, the crystals are treated with acidic aqueous solution such as sulfuric acid, hydrochloric acid or the like to give an aimed crystalline (4R,5S)-trans-5-carboxy-4-(4-fluorophenyl)piperidin-2-one. The optically active amine can be recovered from the remaining acidic aqueous solution by neutralizing the acidic aqueous solution e.g. with sodium hydroxide and extracting with an organic solvent.

The resulting crystals can be filtered and dried for use in the next reduction reaction.

The (4R,5S)-trans-5-carboxy-4-(4-fluorophenyl) piperidin-2-one can be reduced to give (3S,4R)-trans-4-(4-fluorophenyl)-3-hydroxymethylpiperidine represented by the formula (II):

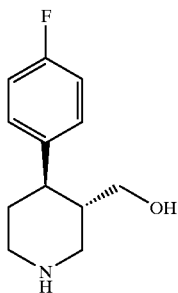

(II)

Upon the reduction reaction, a metal hydride compound (reducing agent) such as diborane, borane complex, boron hydride compound generated from sodium boron hydride in situ, or aluminum hydride compound such as aluminum hydride, diisobutylaluminum hydride or lithium aluminum hydride can be used. It is desired that the amount of the metal hydride compound to be used is usually 6 to 12 equivalents as an active hydride per 1 equivalent of the (4R,5S)-trans-5-carboxy-4-(4-fluorophenyl)piperidin-2-one. There can be employed conventional reducing conditions where a carboxylic acid is reduced to a primary alcohol That is, as a reaction solvent, there can be employed, for example, an ether solvent such as tetrahydrofuran (THF), and a mixed solvent of the ether solvent and a hydrocarbon solvent such as toluene. The reaction temperature can be, for example, within a range of ordinary temperature to 100° C. Upon reaction, for example, when the aluminum hydride compound is used, the reaction is desirably carried out by adding dropwise the (4R,5S)-trans-5-carboxy-4-(4-fluorophenyl)piperidin-2-one thereto.

Alternatively, (4RS,5SR)-trans-4-(4-fluorophenyl)-5-alkoxycarbonylpiperidin-2-one obtained by isomerizing (±)-cis, trans-4-(4-fluorophenyl)-5-alkoxycarbonylpiperidin-2-one represented by the general formula (IX) in the presence of a base can be reduced with a metal hydride reducing agent to give (3SR,4RS)-trans-4-(4-fluorophenyl)-3-hydroxymethylpiperidine. Thereafter, the (3SR,4RS)-trans-4-(4-fluorophenyl)-3-hydroxymethylpiperidine can be optically resolved with an optically active organic acid to give an optically active compound represented by the formula (II).

As the metal hydride reducing agent, there can be exemplified those used for reducing the (4R,5S)-trans-5-carboxy-4-(4-fluorophenyl)piperidin-2-one.

As the optically active organic acid, there can be used, o-chlorotartranilic acid described in J. Org. Chem., 33, 3993 (1968), and the like.

As the conditions such as the amount of the optically active acid to be used, and kinds of the solvent used for resolution and the amount thereof, those used for the optical resolution of the (4RS,5SR)-trans-5-carboxy-4-(4-fluorophenyl)piperidin-2-one can be employed. In addition, as a solvent, water or a mixture of water and acetone can be used.

From (3S,4R)-trans-4-(4-fluorophenyl)-3-hydroxymethylpiperidine thus obtained represented by the formula (II), the piperidine derivative represented by the general formula (I) of the present invention where Z represents methylene group can be obtained as follows:

First, a process for preparing the piperidine derivative represented by the general formula (I) wherein $R^1$ is benzyloxycarbonyl group and Z is methylene group is explained.

The compound (3S,4R)-trans-4-(4-fluorophenyl)-3-hydroxymethylpiperidine represented by the formula (II) can be reacted with a protective reagent represented by the general formula (III):

(III)

wherein $R^3$ is benzyl group and Y is chlorine atom, to give a carbamate compound represented by the general formula (IV):

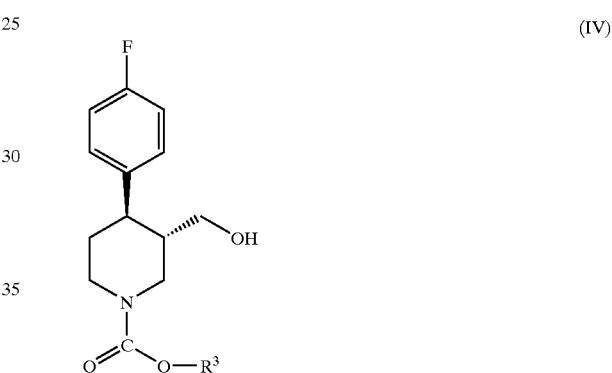

(IV)

wherein $R^3$ is benzyl group.

The above reaction can be carried out, for example, by reacting (3S,4R)-trans-4-(4-fluorophenyl)-3-hydroxymethylpiperidine with the protective reagent represented by the general formula (III) in the presence of a base such as an aqueous sodium bicarbonate solution, but this process does not limit the scope of the present invention.

The carbamate compound represented by the general formula (IV) can be reacted with an organosulfonic acid chloride represented by the general formula (V):

(V)

wherein $R^4$ is an alkyl group having 1 to 2 carbon atoms or phenyl group which may have methyl group at the 4-position, for example, in the presence of an acid acceptor such as triethylamine, to give an organosulfonic acid ester represented by the general formula (VI):

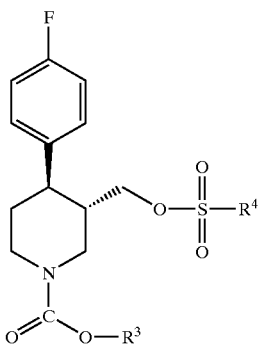

(VI)

wherein $R^3$ is benzyl group, and $R^4$ is methyl group, ethyl group, phenyl group or 4-methylphenyl group.

More specifically, for example, the carbamate compound represented by the general formula (IV) can be reacted with methanesulfonyl chloride in the presence of the acid acceptor to give (3S,4R)-trans-1-benzyloxycarbonyl-4-(4-fluorophenyl)-3-methylsulfonyloxymethylpiperidine represented by the general formula (I), wherein $R^1$ is benzyloxycarbonyl group, $R^2$ is methylsulfonyloxymethyl group, and Z is methylene group.

In addition, for example, the carbamate compound represented by the general formula (IV) can be reacted with ethanesulfonyl chloride, benzenesulfonyl chloride or p-toluenesulfonyl chloride in the presence of the acid acceptor to give (3S,4R)-trans-1-benzyloxycarbonyl-4-(4-fluorophenyl)-3-ethylsulfonyloxymethylpiperidine, (3S,4R)-trans-1-benzyloxycarbonyl-4-(4-fluorophenyl)-3-phenylsulfonyloxymethylpiperidine or (3S,4R)-trans-1-benzyloxycarbonyl-4-(4-fluorophenyl)-3-(4-methylphenyl)sulfonyloxymethylpiperidine represented by the general formula (VI), wherein $R^3$ is benzyl group and $R^4$ is methyl group, phenyl group or 4-methylphenyl group (toluyl group), respectively.

Further, the organosulfonic acid ester represented by the general formula (VI) can be reacted with 3,4-methylenedioxyphenol in the presence of a base to give (3S,4R)-trans-1-benzyloxycarbonyl-4-(4-fluorophenyl)-3-[(3,4-methylenedioxyphenyl)oxymethyl]piperidine represented by the general formula (VII):

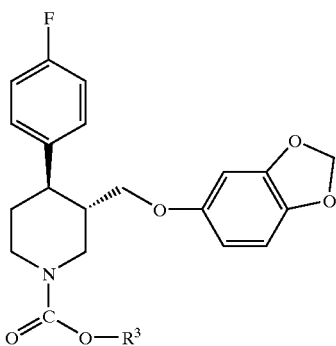

(VII)

wherein $R^3$ is benzyl group, which can also be represented by the general formula (I), wherein $R^1$ is benzyloxycarbonyl group, $R^2$ is 3,4-methylenedioxyphenyloxymethyl group, and Z is methylene group.

Next, a process for preparing the piperidine derivative represented by the general formula (I) wherein $R^1$ is tert-butoxycarbonyl group and Z is methylene group is explained.

When (3S,4R)-trans-4-(4-fluorophenyl)-3-hydroxymethylpiperidine represented by the formula (II) is reacted with di-tert-butyl dicarbonate as a protecting reagent for aminoic nitrogen, it is preferable that 1 to 2 moles of di-tert-butyl dicarbonate is usually used per 1 mole of (3S,4R)-trans-4-(4-fluorophenyl)-3-hydroxymethylpiperidine.

Upon the reaction, a solvent which is unreactive to the (3S,4R)-trans-4-(4-fluorophenyl)-3-hydroxymethylpiperidine and di-tert-butyl dicarbonate can be used.

Examples of the solvent include hydrocarbon solvents represented by toluene, ether solvents represented by tetrahydrofuran, ketone solvents represented by methyl isobutyl ketone, and ester solvents represented by ethyl acetate. Those solvents can be usually used alone or in admixture thereof.

The amount of the solvent to be used is not specified but preferably in the range such that the total amount of the (3S,4R)-trans-4-(4-fluorophenyl)-3-hydroxymethylpiperidine and di-tert-butyl dicarbonate is usually 20 to 100 parts by weight based upon 100 parts by weight of the solvent.

Upon the reaction, a catalyst can be used if necessary. As the catalyst, there can be cited, for example, organic basic catalysts such as tertiary amines such as triethylamine.

The reaction temperature is not limited to specified ones but can be usually within a range of around 0° C. to a boiling point of the solvent.

The reaction atmosphere is not limited to specified ones, but the reaction can be usually carried out in an ambient atmosphere or in an inert gas such as nitrogen gas.

As a result of the reaction, there can be obtained the carbamate compound represented by the general formula (IV) wherein $R^3$ is tert-butyl group.

Then, the resulting carbamate compound represented by the general formula (IV) is reacted with organosulfonic acid chloride represented by the general formula (V).

It is desired that the reaction of the carbamate compound represented by the general formula (IV) with the organosulfonic acid chloride represented by the general formula (V) is usually carried out under the condition such that 0.95 to 1.2 moles of the organosulfonic acid chloride represented by the general formula (V) is used per 1 mole of the starting material (3S,4R)-trans-4-(4-fluorophenyl)-3-hydroxymethylpiperidine.

Upon the reaction of the carbamate compound represented by the general formula (IV) with the organosulfonic acid chloride represented by the general formula (V), the reaction conditions, more specifically, solvent, catalyst, reaction temperature and reaction atmosphere can be the same as those for the reaction of (3S,4R)-trans-4-(4-fluorophenyl)-3-hydroxymethylpiperidine represented by the formula (II) and di-tert-butyl dicarbonate.

In the present invention, after the completion of the reaction of (3S,4R)-trans-4-(4-fluorophenyl)-3-hydroxymethylpiperidine represented by the formula (II) and di-tert-butyl dicarbonate, the successive reaction can be achieved by adding the organosulfonic acid chloride represented by the general formula (V) and an acid acceptor to the reaction mixture if necessary after the removal of the azeotropic water from the reaction mixture.

Thus, there is obtained a carbamate compound represented by the general formula (VI), wherein $R^3$ is benzyl group or tert-butyl group.

Then, the organosulfonic acid ester represented by the general formula (VI) is reacted with 3,4-methylenedioxyphenol in the presence of a base.

It is desired that the amount of 3,4-methylenedioxyphenol to be used is usually 1 to 3 moles or so per 1 mole of the organosulfonic acid ester represented by the general formula (VI).

As a reaction solvent to be used for reacting the organosulfonic acid ester represented by the general formula (VI) with 3,4-methylenedioxyphenol, there can be cited, for example, lower alcohol solvents having 1 to 4 carbon atoms, polar organic solvents such as amide solvents such as dimethylformamide, dimethylacetamide, N-methylpyrrolidone, and dimethyl sulfoxide, and hydrocarbon solvents such as toluene. Those solvents can be usually used alone or in admixture thereof.

The amount of the solvent to be used is not limited to specified ones but is preferably such that the total amount of the organosulfonic acid ester represented by the general formula (VI) and 3,4-methylenedioxyphenol is usually 20 to 100 parts by weight, based upon 100 parts by weight of the solvent.

As the base, there can be cited, for example, sodium hydride, sodium methoxide, sodium amide, potassium tert-butoxide, sodium hydroxide and sodium carbonate.

It is preferable that the amount of the base to be used is usually 0.8 to 1 mole per 1 mole of 3,4-methylenedioxyphenol.

The reaction temperature can be usually within a range of ordinary temperature to the boiling point of the solvent. The reaction can be performed under pressure if necessary.

The reaction atmosphere is not limited to specified ones, but the reaction can be usually carried out in an ambient atmosphere or in an inert gas such as nitrogen gas.

The piperidine derivative (3S,4R)-trans-1-benzyloxycarbonyl-4-(4-fluorophenyl)-3-[(3,4-methylenedioxyphenyl)oxymethyl]piperidine thus obtained, represented by the general formula (VII), wherein $R^3$ is benzyl group, can be catalytically hydrogenolyzed to deprotect a protecting group, i.e. benzyloxycarbonyl group. The deprotection of the benzyloxycarbonyl group can be carried out, for example, as follows:

The (3S,4R)-trans-1-benzyloxycarbonyl-4-(4-fluorophenyl)-3-[(3,4-methylenedioxyphenyl)oxymethyl]-piperidine is dissolved in a solvent and the reaction can be carried out by stirring in hydrogen gas atmosphere in the presence of a catalyst.

As the catalyst, there can be cited, for instance, palladium-carbon, and the like. It is desired that the amount of the catalyst is usually 1 to 10 parts by weight or so based upon 100 parts by weight of the (3S,4R)-trans-1-benzyloxycarbonyl-4-(4-fluorophenyl)-3-[(3,4-methylenedioxyphenyl)oxymethyl]piperidine.

As the solvent, there can be cited, for instance, hydrocarbon solvents such as toluene, ether solvents such as tetrahydrofuran, alcohol solvents such as methanol, and a mixture thereof.

The reaction temperature can be usually within a range of ordinary temperature to 100° C.

The pressure of hydrogen gas to be introduced in the solution is not limited to specified ones but can be usually ordinary atmospheric pressure to around 20 kgf/cm$^2$. It is desired that the amount of hydrogen gas to be introduced in the solution is usually at least 1 mole per 1 mole of the (3S,4R)-trans-1-benzyloxycarbonyl-4-(4-fluorophenyl)-3-[(3,4-methylenedioxyphenyl)oxymethyl]-piperidine.

The reaction time is not limited to specified ones but can be a time until the completion of the reaction. The completion of the reaction can be monitored, for example, by chromatography and can be a point at which the (3S,4R)-trans-1-benzyloxycarbonyl-4-(4-fluorophenyl)-3-[(3,4-methylenedioxyphenyl)oxymethyl]piperidine disappears.

Thus, (3S,4R)-trans-4-(4-fluorophenyl)-3-[(3,4-methylenedioxyphenyl)oxymethyl]piperidine is obtained.

After (3S,4R)-trans-1-benzyloxycarbonyl-4-(4-fluorophenyl)-3-[(3,4-methylenedioxyphenyl)oxymethyl]-piperidine is catalytically hydrogenolyzed to deprotect benzyloxycarbonyl group, hydrogen chloride can be added thereto to give (3S,4R)-trans-4-(4-fluorophenyl)-3-[(3,4-methylenedioxyphenyl)oxymethyl]piperidine hydrochloride. When hydrogen chloride is reacted on the (3S,4R)-trans-4-(4-fluorophenyl)-3-[(3,4-methylenedioxyphenyl)oxymethyl]-piperidine in a nonaqueous anhydrous solvent, anhydrous (3S,4R)-trans-4-(4-fluorophenyl)-3-[(3,4-methylenedioxyphenyl)oxymethyl]piperidine hydrochloride is obtained, which is useful as an antidepressant.

As a method for preparing anhydrous hydrochloride of the (3S,4R)-trans-4-(4-fluorophenyl)-3-[(3,4-methylenedioxyphenyl)oxymethyl]piperidine from the (3S,4R)-trans-4-(4-fluorophenyl)-3-[(3,4-methylenedioxyphenyl)oxymethyl]piperidine, there can be employed, for example, the following method.

The (3S,4R)-trans-4-(4-fluorophenyl)-3-[(3,4-methylenedioxyphenyl)oxymethyl]piperidine is first dissolved in a nonaqueous solvent.

As the non-aqueous solvent, there can be cited, for instance, hydrocarbon solvents such as toluene, ester solvents such as ethyl acetate, ether solvents such as tetrahydrofuran, halogenated solvents such as dichloromethane, alcohol solvents such as ethanol and isopropanol, and a mixture thereof.

Then, hydrogen chloride gas is introduced in the resulting solution. The use of dry hydrogen chloride gas is preferable from the viewpoint that the incorporation of moisture in the reaction system is avoided. In the present invention, a nonaqueous solvent containing hydrogen chloride in it can be added to the solution.

It is desired that the amount of hydrogen chloride to be introduced in the solution is usually at least 1 mole per 1 mole of the (3S,4R)-trans-4-(4-fluorophenyl)-3-[(3,4-methylenedioxyphenyl)oxymethyl]piperidine.

The reaction temperature can be usually within a range of ordinary temperature to the boiling point of the solvent.

The reaction time is not limited to specified ones but can be a time until the completion of the reaction. The completion of the reaction can be a point at which the weight of absorbed hydrogen chloride reaches a required amount.

Next, the deprotection of tert-butoxycarbonyl group of the (3S,4R)-trans-1-tert-butoxycarbonyl-4-(4-fluorophenyl)-3-[(3,4-methylenedioxyphenyl)oxymethyl]-piperidine represented by the general formula (VII), wherein $R^3$ is tert-butyl group can be carried out by reacting hydrogen chloride on (3S,4R)-trans-1-tert-butoxycarbonyl-4-(4-fluorophenyl)-3-[(3,4-methylenedioxyphenyl)oxymethyl]piperidine in isopropanol to give (3S,4R)-trans-4-(4-fluorophenyl)-3-[(3,4-methylenedioxyphenyl)oxymethyl]piperidine hydrochloride. This reaction is a reaction for deprotecting tert-butoxycarbonyl group.

The amount of (3S,4R)-trans-1-tert-butoxycarbonyl-4-(4-fluorophenyl)-3-[(3,4-methylenedioxyphenyl)oxymethyl]-piperidine to be mixed with isopropanol is not limited to specified ones, but usually the amount is preferably 5 to 50 parts by weight based upon 100 parts by weight of the isopropanol.

It is desired that the amount of hydrogen chloride to react on (3S,4R)-trans-1-tert-butoxycarbonyl-4-(4-fluorophenyl)-3-[(3,4-methylenedioxyphenyl)oxymethyl]-piperidine is usually 1 to 5 moles per 1 mole of (3S,4R)-trans-1-tert-butoxycarbonyl-4-(4-fluorophenyl)-3-[(3,4-methylenedioxyphenyl)oxymethyl]piperidine.

In the present invention, for example, other organic solvent and organic acid may be conveniently added thereto in an amount so as not to impair the object of the present invention.

As the method for reacting hydrogen chloride thereon, there can be cited, for instance, a method of first dissolving hydrogen chloride in isopropanol, and adding the (3S,4R)-trans-1-tert-butoxycarbonyl-4-(4-fluorophenyl)-3-[(3,4-methylenedioxyphenyl)oxymethyl]-piperidine thereto while stirring, a method of introducing hydrogen chloride gas into a solution obtained by dissolving the (3S,4R)-trans-1-tert-butoxycarbonyl-4-(4-fluorophenyl)-3-[(3,4-methylenedioxyphenyl)oxymethyl]-piperidine in isopropanol, or a method of adding a solution obtained by dissolving hydrogen chloride gas in isopropanol to the above (3S,4R)-trans-1-tert-butoxycarbonyl-4-(4-fluorophenyl)-3-[(3,4-methylenedioxyphenyl)oxymethyl]piperidine while stirring, and the like.

The temperature when hydrogen chloride is reacted thereon varies depending upon the amount of hydrogen chloride used and is usually within a range of ordinary temperature to the boiling point of isopropanol when the amount of hydrogen chloride is within a range of 1 to 2 mole per 1 mole of the (3S,4R)-trans-1-tert-butoxycarbonyl-4-(4-fluorophenyl)-3-[(3,4-methylenedioxyphenyl)oxymethyl] piperidine.

When the hydrogen chloride is reacted thereon, (3S,4R)-trans-1-tert-butoxycarbonyl-4-(4-fluorophenyl)-3-[(3,4-methylenedioxyphenyl)oxymethyl]piperidine hydrochloride is formed, at the same time that the tert-butoxycarbonyl group is deprotected.

The (3S,4R)-trans-4-(4-fluorophenyl)-3-[(3,4-methylenedioxyphenyl)oxymethyl]piperidine hydrochloride isopropanol solution thus obtained contains impurities in some cases. In this case, the isopropanol solution can be treated with activated carbon to remove the impurities.

Next, the isopropanol solution is gradually cooled to obtain crystals of (3S,4R)-trans-4-(4-fluorophenyl)-3-[(3,4-methylenedioxyphenyl)oxymethyl]piperidine hydrochloride having good filtration properties.

Usually, isopropanol is incorporated in a content of 8 to 15% by weight in the thus obtained crystals of (3S,4R)-trans-4-(4-fluorophenyl)-3-[(3,4-methylenedioxyphenyl) oxymethyl]piperidine hydrochloride.

The crystals of the (3S,4R)-trans-4-(4-fluorophenyl)-3-[(3,4-methylenedioxyphenyl)oxymethyl]piperidine hydrochloride are dried, for example, at 80° to 110° C. under reduced pressure to convert the crystals from those having the maximum endothermic peak at a temperature range of 98° to 110° C. to those having the maximum endothermic peak at a temperature range of 118° to 132° C. as measured by DSC (differential scanning calorimetry). The reason why the heating temperature is adjusted to not lower than 80° C. is to rapidly dry isopropanol. The reason why the heating temperature is adjusted to not higher than 110° C. is to avoid melting of the crystals.

The crystals thus converted are composed of anhydrous (3S,4R)-trans-4-(4-fluorophenyl)-3-[(3,4-methylenedioxyphenyl)oxymethyl]piperidine hydrochloride having an isopropanol content of 0.1 to 5% by weight.

The anhydrous hydrochloride is a compound useful as an antidepressant.

EXAMPLES

The present invention will be described in the following working examples, without intending to restrict the scope of the present invention thereto.

The anhydrous paroxetine hydrochloride containing isopropanol in the crystals, which is mentioned in some of the following examples, is disclosed, for instance, in Japanese Examined Patent Publication No. 6-47587 (U.S. Pat. No. 4,721,723) and International Journal of Pharmaceutics, 42, (1988), pp.135–143.

Example 1

A 300-ml four-necked glass flask equipped with a thermometer, a reflux condenser, and a dropping funnel was charged with 150 ml of methanol, 33.0 g (183 mmol) of methyl p-fluorocinnamate, 36.3 g (366 mmol) of methyl cyanoacetate, and 52.96 g (275 mmol) of 28%-methanol solution of sodium methylate, while stirring. Thereafter, the resulting mixture was heated to a reflux temperature and kept at the temperature for additional 90 minutes. The reaction mixture was then concentrated by removing the solvent using a rotary evaporator.

The concentrated mixture obtained above was poured into a mixture of 150 ml of toluene and 200 ml of 5%-aqueous hydrochloric acid. The whole mixture was stirred, and then allowed to stand to separate into organic and aqueous layers, and the aqueous layer was removed therefrom. The organic layer was washed with a 100-ml aliquot of a saturated aqueous sodium bicarbonate solution twice, and subsequently washed with 100 ml of water. Thereafter, the organic layer was dried over anhydrous sodium sulfate, and then the solvent was removed under a reduced pressure using a rotary evaporator to concentrate the organic layer.

The concentrate was distilled to give dimethyl 2-cyano-3-(4-fluorophenyl)glutarate having a boiling point of 168° to 170° C. (4 mmHg). The yield was 82.7% based on methyl p-fluorocinnamate. A portion of the product was recrystallized from methanol, to give crystals having a melting point of 80.2° C.

Example 2

A 300-ml four-necked glass flask equipped with a thermometer, a reflux condenser, and a dropping funnel was charged with 90 ml of methyl acetate and 10.5 g (194.4 mmol) of sodium methylate. To the resulting slurry, a mixed solution of 10 ml of methyl acetate and 10.0 g (80.6 mmol) of p-fluorobenzaldehyde was added, while stirring, dropwise over a period of 30 minutes at a temperature of from 10° to 20° C., and further stirred for additional 30 minutes at the same temperature, and then a mixed solution of 20 ml of methyl acetate and 11.9 g (120 mmol) of methyl cyanoacetate was added dropwise to the above mixture over a period of 45 minutes at a temperature of from 10° to 20° C. After the dropwise addition was completed, the resulting mixture was stirred for additional 13 hours at a temperature of from 57° to 58° C. The resulting mixture was poured into a mixture of 100 ml of toluene and 150 ml of 5%-aqueous hydrochloric acid, while stirring, and then allowed to stand to separate into organic and aqueous layers, and the aqueous layer was removed therefrom. The organic layer was washed with a 100-ml aliquot of a saturated aqueous sodium bicarbonate solution twice, and subsequently washed with 100 ml of water. Thereafter, the organic layer was dried over anhydrous sodium sulfate, and then the solvent was removed under a reduced pressure using a rotary evaporator to concentrate the organic layer.

The concentrate was distilled to give dimethyl 2-cyano-3-(4-fluorophenyl)glutarate having a boiling point of from 168° to 170° C. (4 mmHg). The yield was 69.3% based on p-fluorobenzaldehyde.

Example 3

A 500-ml autoclave was charged with 200 ml of methanol, 10.0 g (35.8 mmol) of dimethyl 2-cyano-3-(4-fluorophenyl)glutarate prepared in either Example 1 or 2, and 1.0 ml of Raney cobalt catalyst, and then hydrogen gas was introduced into the autoclave under the conditions of pressure 15 to 17 kgf/cm$^2$ and reaction temperature 85° to 95° C. to the above autoclave. Thereafter, the resulting mixture was stirred for one hour under the same conditions as given above, and then the obtained mixture was cooled to a temperature of from 20° to 30° C. Subsequently, after adjusting the pressure to a normal pressure, the reaction mixture was filtered to remove the catalyst, and then the filtrate was concentrated by removing methanol using a rotary evaporator under a reduced pressure, to give 8.97 g of crude crystals of (±)-trans-4-(4-fluorophenyl)-5-methoxycarbonylpiperidin-2-one.

50 ml of toluene was added to the crude crystals prepared above, and then the resulting mixture was sufficiently mixed. Thereafter, the crystals were collected by filtration, and then the crystals were air-dried, to give 6.55 g of white crystals of (±)-trans-4-(4-fluorophenyl)-5-methoxycarbonylpiperidin-2-one. The yield was 72.8% based on dimethyl 2-cyano-3-(4-fluorophenyl)glutarate.

Example 4

A 200-ml four-necked glass flask equipped with a thermometer and a reflux condenser was charged with 50 ml of methanol, 10.0 g (39.8 mmol) of (±)-trans-4-(4-fluorophenyl)-5-methoxycarbonylpiperidin-2-one prepared in Example 3, and 1.75 g (43.8 mmol) of sodium hydroxide, and the mixture was heated while stirring to the reflux temperature, and kept at the reflux temperature for additional four hours. Subsequently, the reaction mixture was cooled to a temperature of from 0° to 10° C., and 90 ml of 2%-aqueous hydrochloric acid was added thereto, to allow white crystals to precipitate.

The crystals were then collected by filtration, and sufficiently washed with water. Thereafter, the obtained crystals were dried at 60° C. under a reduced pressure, to give 8.26 g of the white crystals of (±)-trans-5-carboxy-4-(4-fluorophenyl)piperidin-2-one. The yield was 87.5% based on (±)-trans-4-(4-fluorophenyl)-5-methoxycarbonylpiperidin-2-one.

The physical properties of the white crystals prepared in Example 4 were as follows.

(1) Melting point: 246° C.
(2) IR (KBr) ν(cm$^{-1}$): 2400–3700, 1710, 1638, 1508, 1208.
(3) $^1$H-NMR ((CD$_3$)$_2$SO) δ (ppm): 2.32–2.58 (m, 1H), 2.60–2.68 (m, 1H), 3.05–3.18 (m, 1H), 3.30–3.58 (m, 3H), 7.19–7.52 (m, 4H), 12.52 (br s, 1H).

Example 5

In order to separate the cis isomer contained in the crude crystals of (±)-trans-4-(4-fluorophenyl)-5-methoxycarbonylpiperidin-2-one prepared in Example 3, about 5 g of the crude crystals were added to about 30 ml of methanol, and the mixture was heated to a reflux temperature. Soon after, the mixture was gradually cooled using crystals, which remained in the solution without being completely dissolved, as seed crystals, to precipitate crystals having a nearly cubic shape. Since needle crystals would be formed if the crystallization was continued, the cubic crystals were separated from the solution before the beginning of the formation of the needle crystals. The resulting cubic crystals were recrystallized again from methanol, to give (±)-cis-4-(4-fluorophenyl)-5-methoxycarbonylpiperidin-2-one.

The physical properties of the cubic crystals prepared above were as follows.

(1) Melting point: 195.0° to 196.5° C.
(2) IR (nujol mull) ν(cm$^{-1}$): 3184, 3036, 1736, 1662, 1600, 1510, 1248.
(3) $^1$H-NMR (CDCl$_3$) δ (ppm): 2.72–3.91 (m, 2H), 3.08–3.40 (m, 1H), 3.35–3.57 (m, 2H), 3.65 (s, 3H), 3.67–3.82 (m, 1H), 6.51 (br s, 1H), 6.95–7.25 (m, 4H).

The solution separated from the cubic crystals was allowed to crystallize, to give needle crystals of (±)-trans-4-(4-fluorophenyl)-5-methoxycarbonylpiperidin-2-one, and then the crystals were recrystallized from methanol.

The physical properties of the needle crystals prepared above were as follows.

(1) Melting point: 152.2° to 152.3° C. (Shrinkage of the crystals was observed in the tube for measuring a melting point from a temperature near 150° C.).
(2) IR (nujol mull) ν(cm$^{-1}$): 3172, 3036, 1728, 1672, 1604, 1512, 1220.
(3) $^1$H-NMR (CDCl$_3$) δ (ppm): 2.55 (dd, 1H, J=17.8, 10.6), 2.69 (dd, 1H, J=17.8, 5.9), 2.95 (dt, 1H, J=5.3, 9.9), 3.41 (dt, 1H, J=5.9, 10.3), 3.45–3.71 (m, 2H), 3.50 (s, 3H), 6.85 (br s, 1H), 6.99–7.25 (m, 4H).

The physical properties of the purified crystals of (±)-trans-4-(4-fluorophenyl)-5-ethoxycarbonylpiperidin-2-one prepared in the same manner as above were as follows.

(1) Melting point: 143.8° C.
(2) IR (KBr) ν(cm$^{-1}$): 3180, 3044, 1720, 1662, 1606, 1228, 1206.
(3) $^1$H-NMR (CDCl$_3$) δ (ppm): 0.99 (t, 3H, J=7.3), 2.55 (dd, 2H, J=17.8, 10.6), 2.69 (dd, 2H, J=17.8, 5.9), 2.95 (dt, 1H, J=5.3, 9.9), 3.36 (dt, 1H, J=5.9, 10.6), 3.48–3.68 (m, 1H), 3.63 (dd, 1H, J=9.9, 10.6), 3.87–4.02 (m, 1H), 6.31 (br s, 1H), 6.95–7.22 (m, 4H).

Example 6

50 mg of (±)-cis-4-(4-fluorophenyl)-5-methoxycarbonylpiperidin-2-one prepared in Example 5 was added to 4 g of methanol. Thereafter, 100 mg of 10%-aqueous sodium hydroxide solution was added to the above mixture, and the resulting mixture was heated and refluxed over a period of three hours. After cooling the reaction mixture, the methanol solution was concentrated under a reduced pressure. Subsequently, water was added to the concentrate, and then the reaction mixture was extracted with ethyl acetate to remove a neutral portion. An aqueous hydrochloric acid was added to the aqueous layer to make it acidic. Thereafter, the acidic aqueous layer was extracted with ethyl acetate and then concentrated to give about 40 mg of crystals. IR spectroscopy of the crystals which were prepared by washing the above crystals with a small amount of ethyl acetate was found to be identical to that of (±)-trans-5-carboxy-4-(4-fluorophenyl)piperidin-2-one obtained in Example 4.

The same procedures as above were carried out except for adding a catalytic amount of 60%-sodium hydride (dispersion in mineral oil) to obtain sodium methylate solution in place of adding the aqueous sodium hydroxide solution, and 50 mg of (±)-cis-4-(4-fluorophenyl)-5-methoxycarbonylpiperidin-2-one was heated and refluxed over a period of three hours. After cooling the reaction mixture, the mixture was concentrated under a reduced pressure. Thereafter, water was added to the concentrate, and the obtained mixture was extracted with ethyl acetate. The extracted neutral part was concentrated to give about 40 mg of crystals. IR spectroscopy of the crystals prepared by washing the above crystals with a small amount of methanol was found to be identical to that of (±)-trans-4-(4-fluorophenyl)-5-methoxycarbonylpiperidin-2-one obtained in Example 3.

Further, the conversion of methyl esters of the (±)-cis, trans isomers to methyl ester of (±)-trans isomer was carried out by the following method.

Specifically, 30 g of (±)-cis-, trans-4-(4-fluorophenyl)-5-methoxycarbonylpiperidin-2-one and 2.34 g of a 28% sodium methylate methanol solution were added to 300 ml of toluene, and the mixture was heated. When the temperature reached 68° C., the (±)-cis-, trans-4-(4-fluorophenyl)-5-methoxycarbonylpiperidin-2-one dissolved. The solution was stirred for additional 20 minutes, and gradually cooled and filtered at 7° C. to give 25.23 g of (±)-trans-4-(4-fluorophenyl)-5-methoxycarbonylpiperidin-2-one (yield: 84.1%).

The obtained crystals of methyl ester of (±)-trans isomer were analyzed by high performance liquid chromatography. The results showed that methyl ester of the trans isomer made up 98.75% of the entire products, and substantially no cis isomers were formed, and that the remaining 1.25% was made up of trans isomer of carboxylic acid.

Reference Example

The stereostructure (geometric isomers) of the piperidine derivatives represented by the formula:

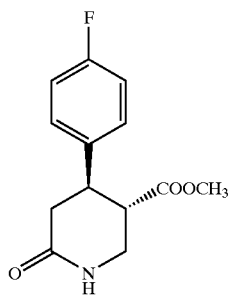

was confirmed as follows.

A 50-ml eggplant-shaped glass flask was charged with about 10 mg of toluene and 1 g of pyridine. 0.9 g Of (±)-trans-3-hydroxymethyl-4-(4-fluorophenyl)-N-methylpiperidine (hereinafter referred to as "Known Compound A"), which was prepared according to the method disclosed in Japanese Unexamined Patent Publication No. 7-138228 was added to and dissolved in the above mixture. After the mixture was cooled to a temperature of −20° C., a mixed solution prepared by dissolving 0.52 g of ethyl chloroformate in about 5 ml of toluene was added dropwise thereto. The temperature of the resulting mixture was gradually raised to room temperature, and then allowed to stand at room temperature for about two hours. Thereafter, about 10 ml of water was added to the above mixture, and then the mixture was made alkaline by adding aqueous sodium hydroxide solution. The alkaline mixture was allowed to stand to separate into a toluene layer and an aqueous layer, and the aqueous layer was removed. The toluene layer was concentrated by using a rotary evaporator, and the remaining concentrate (hereinafter referred to as "Derivative B") was obtained as an oily product. Further, about 5 ml of toluene was again added to Derivative B, and 1 g of ethyl chloroformate was added to the above mixture at room temperature. Thereafter, the resulting mixture was allowed to stand overnight. Subsequently, diluted aqueous hydrochloric acid was added thereto, and the toluene solution was separated therefrom as the neutral part. The separated toluene solution was then concentrated with a rotary evaporator, to give an oily product of (±)-trans-3-ethoxycarbonyloxymethyl-4-(4-fluorophenyl)-N-ethoxycarbonylpiperidine (hereinafter referred to as "Derivative C").

On the other hand, a 100-ml four-necked glass flask was charged with 20 ml of dry diglyme containing 0.5 g of lithium aluminum hydride, and 0.2 g of crystals of (±)-trans-4-(4-fluorophenyl)-5-methoxycarbonylpiperidin-2-one was added to the above mixture at room temperature. Thereafter, the resulting mixture was heated to about 100° C. and kept at the temperature for one hour. After cooling the reaction mixture, 10 ml of 28%-aqueous sodium hydroxide solution was added dropwise to the above mixture. Thereafter, the upper organic layer was separated from the lower layer having a high viscosity by decantation. Subsequently, the lower layer was extracted with tetrahydrofuran (THF) and the THF part was combined with the upper organic layer. Further, the solvent was removed, to give 0.2 g of a concentrate. The resulting concentrate crystallized. The resulting product is hereinafter referred to as "Derivative D."

The melting point of Derivative D, which was prepared separately in the same manner as above and recrystallized from ethyl acetate was 103.2° to 104.0° C.

The reduced product (Derivative D) prepared above was dissolved in 10 ml of pyridine, and the mixture was cooled to −10° C. The solution of 0.5 g of ethyl chloroformate in about 5 ml of toluene was added dropwise to the cooled mixture. Thereafter, the temperature of the mixture was allowed to rise to room temperature and kept at room temperature for one hour. Subsequently, water was added to the above mixture, and extracted with toluene. Thereafter, the toluene extract was concentrated to give 0.2 g of an oily product (hereinafter referred to as "Derivative E"). It was confirmed by the $^1$H-NMR spectroscopy and the high performance liquid chromatography that the obtained product was identical to Derivative C, that is, (±)-trans-3-ethoxycarbonyloxymethyl-4-(4-fluorophenyl)-N-ethoxycarbonylpiperidine which was derived from (±)-trans-3-hydroxymethyl-4-(4-fluorophenyl)-N-methylpiperidine prepared by the method disclosed in Japanese Unexamined Patent Publication No. 7-138228.

Further, in order to obtain a crystalline compound, a part of Derivative E was reduced with excess lithium aluminum hydride in the same manner as above. As a result, a reduced product (hereinafter referred to as "Derivative F") was obtained. The resulting reduced product was purified by silica gel chromatography, and then the part eluted by ethyl acetate containing methanol crystallized. The crystals showed the same physical properties as the (±)-trans-3-hydroxymethyl-4-(4-fluorophenyl)-N-methylpiperidine (Known Compound A) prepared by the method disclosed in Japanese Unexamined Patent Publication No. 7-138228 as follows.

(1) Melting point: 122.5° to 122.9° C.

(2) IR (nujol mull) ν(cm$^{-1}$): 3144, 1600, 1466, 1450, 1066.

From the above results, it is clear that the stereostructure of the compound which was designated as "trans isomer" of the piperidine derivatives represented by the preceding formula was identical to that of the (±)-trans-3-hydroxymethyl-4-(4-fluorophenyl)-N-methylpiperidine.

Example 7

A 3000-ml four-necked glass flask equipped with a thermometer, a reflux condenser, and a dropping funnel was charged with 1560 ml of isopropanol, 473 ml of ethanol, and 35.58 g (150 mmol) of (4RS,5SR)-trans-5-carboxy-4-(4-fluorophenyl)piperidin-2-one, and the mixture was stirred and heated to a temperature of from 70° to 75° C.

While maintaining the temperature of the mixture at a temperature of from 70° to 75° C., 72.14 g of an ethanol solution containing 34.48 g (151.7 mmol) of R-(+)-N-(4-hydroxyphenylmethyl)phenylethylamine was added dropwise to the mixture. The temperature of the mixture was then kept at a temperature of from 80° to 81° C. for one hour while stirring. Thereafter, the reaction mixture was cooled to 25° C., and stirred for additional two hours at a temperature of from 20° to 25° C. to allow crystals to precipitate.

Next, the precipitated crystals were filtered at a temperature of from 20° to 25° C., and then the crystals were washed with the mixture of 60 ml of isopropanol and 18 ml of ethanol. Thereafter, the crystals were dried under a reduced pressure, to give 32.76 g of crystals, which were a salt of (4R,5S)-trans-5-carboxy-4-(4-fluorophenyl)piperidin-2-one and R-(±)-N-(4-hydroxyphenylmethyl)phenylethylamine. 5 mg Of the above crystals was taken, and 5 ml of 3%-aqueous hydrochloric acid was added thereto, to allow acid decomposition, to give (4R,5S)-trans-5-carboxy-4-(4-fluorophenyl)piperidin-2-one.

Further, the resulting crystals were analyzed by high performance liquid chromatography using a chiral HPLC column. The results showed that the crystals were composed of 15.5% of the (4S,5R) isomer, and 84.5% of the (4R,5S) isomer, and the optical purity was 69.0%.

Thereafter, 32.76 g of the resulting crystals were added to 350 ml of methanol, and the obtained mixture was heated to 65° C. 10 ml Of water was added to the resulting mixture at 65° C., and the mixture was stirred to dissolve the crystals. Subsequently, the reaction mixture was stirred for additional one hour at a temperature of from 57° to 58° C., and then 5 mg of seed crystals, which were a salt of (4R,5S)-trans-5-carboxy-4-(4-fluorophenyl)piperidin-2-one and R-(+)-N-(4-hydroxyphenylmethyl)phenylethylamine was added to the above mixture, and then the resulting mixture was stirred for additional one hour at a temperature of from 57° to 58° C. Thereafter, the mixture was cooled to 50° C., and then 200 ml of ethyl acetate was added at a temperature of from 47° to 50° C. Further, the mixture was stirred for one hour and 30 minutes at a temperature of from 47° to 50° C.

Further, the mixture was cooled to 25° C., and stirred for additional two hours at a temperature of from 20° to 25° C. to allow crystals to precipitate. Thereafter, the precipitated crystals were collected by filtration at a temperature of from 20° to 25° C., and washed with a mixed solvent of 40 ml of methanol and 20 ml of ethyl acetate. Subsequently, the washed crystals were dried under a reduced pressure, to give 17.21 g of crystals, which were a salt of (4R,5S)-trans-5-carboxy-4-(4-fluorophenyl)piperidin-2-one and R-(+)-N-(4-hydroxyphenylmethyl)phenylethylamine. 100 ml Of 3%-aqueous hydrochloric acid was added to 17.21 g of the above crystals, to allow acid decomposition. The crystals were collected by filtration, and washed with water and then dried under a reduced pressure, to give 8.97 g of crystals, which were (4R,5S)-trans-5-carboxy-4-(4-fluorophenyl)piperidin-2-one.

Further, the resulting crystals were analyzed by high performance liquid chromatography using a chiral HPLC column. The results showed that the crystals were composed of 0.4% of the (4S,5R) isomers, and 99.6% of the (4R,5S) isomers, and the optical purity was 99.2%. The physical properties of the resulting crystals were as follows.

(1) Melting point: 236° to 238° C.
(2) IR (nujol mull) ν(cm$^{-1}$): 3276, 3200, 1704, 1640, 1512, 1404, 1298, 1270, 1208, 1194, 1042, 982, 826, 780.

Example 8

A 1000-ml four-necked glass flask equipped with a thermometer, a reflux condenser, and a dropping funnel was charged with 1670 ml of isopropanol, 30.0 g (126.5 mmol) of (4RS,5SR)-trans-5-carboxy-4-(4-fluorophenyl)piperidin-2-one, and 35 ml of water, and the mixture was stirred and heated to a temperature of from 77° to 82° C.

While maintaining the temperature of the mixture at a temperature of from 77° to 82° C., 90 ml of an isopropanol solution of 29.16 g (128.3 mmol) of R-(+)-N-(4-hydroxyphenylmethyl)phenylethylamine was added dropwise to the mixture prepared above.

Subsequently, 5 mg of seed crystals, which were a salt of (4R,5S)-trans-5-carboxy-4-(4-fluorophenyl)piperidin-2-one and R-(+)-N-(4-hydroxyphenylmethyl)phenylethylamine were added to the above mixture at 75° C., and then the resulting mixture was stirred for additional one hour at a temperature of from 70° to 75° C. Thereafter, the mixture was cooled to 25° C. and then stirred for two hours at a temperature of from 20° to 25° C. to allow crystals to precipitate. Next, the precipitated crystals were collected by filtration at a temperature of from 20° to 25° C., and washed with 30 ml of isopropanol. Thereafter, the washed crystals were dried under a reduced pressure, to give 27.74 g of crystals, which were a salt of (4R,5S)-trans-5-carboxy-4-(4-fluorophenyl)piperidin-2-one and R-(±)-N-(4-hydroxyphenylmethyl)phenylethylamine.

A part of the above crystals, namely 5 g, was taken, and 5 ml of 3%-aqueous hydrochloric acid was added thereto, to allow acid decomposition, to give crystals of (4R,5S)-trans-5-carboxy-4-(4-fluorophenyl)piperidin-2-one.

Further, the resulting crystals were analyzed by high performance liquid chromatography using a chiral HPLC column. The results showed that the crystals, which were composed of 8.3% of the (4S,5R) isomer, and 91.7% of the (4R,5S) isomer, and the optical purity was 83.49%.

Thereafter, 26.82 g of the resulting crystals were added to 350 ml of isopropanol, and the obtained mixture was heated to 77° C. 55 ml Of water was added to the resulting mixture at 77° C., and the mixture was stirred to dissolve the crystals. Subsequently, the mixture was stirred for additional one hour at a temperature of from 77° to 82° C., and then 3 mg of seed crystals, which were a salt of (4R,5S)-trans-5-carboxy-4-(4-fluorophenyl)piperidin-2-one and R-(+)-N-(4-hydroxyphenylmethyl)phenylethylamine was added to the above mixture. Thereafter, the mixture was cooled to 55° C., and stirred for additional one hour at a temperature of from 55° to 60° C. Thereafter, the mixture was cooled to 25° C., and stirred for two hours at a temperature of from 20° to 25° C. to allow crystals to precipitate.

Further, the precipitated crystals were collected by filtration at a temperature of from 20° to 25° C., and washed with 20 ml of 85%-aqueous isopropanol. Subsequently, the washed crystals were dried under a reduced pressure, to give 16.60 g of crystals, which were a salt of (4R,5S)-trans-5-carboxy-4-(4-fluorophenyl)piperidin-2-one and R-(±)-N-(4-hydroxyphenylmethyl)phenylethylamine. 100 ml Of 3%-aqueous hydrochloric acid was added to 16.60 g of the above crystals, and the resulting mixture was stirred at a temperature of 20° to 40° C., to allow acid decomposition. Thereafter, the resulting crystals were collected by filtration, and washed with water. Subsequently, the washed crystals were dried under a reduced pressure, to give 8.28 g of crystals, which were (4R,5S)-trans-5-carboxy-4-(4-fluorophenyl)piperidin-2-one.

Further, the resulting crystals were analyzed by high performance liquid chromatography using a chiral HPLC column. The results showed that the crystals were composed of 0.4% of the (4S,5R) isomer, and 99.6% of the (4R,5S) isomer, and the optical purity was 99.2%.

Example 9

A 300-ml four-necked glass flask equipped with a thermometer, a reflux condenser, and a dropping funnel was charged with 100 ml of anhydrous tetrahydrofuran and 7.89 g (208.02 mmol) of lithium aluminum hydride, and the slurry mixture was cooled to a temperature of from 5° to 10° C.

To the above slurry, slurry prepared from 16.34 g (69.34 mmol) of (4R,5S)-trans-5-carboxy-4-(4-fluorophenyl)piperidin-2-one and 100 ml of tetrahydrofuran was cautiously added dropwise at a temperature of from 10° to 20° C. After the completion of dropwise addition, the resulting mixture was stirred at a temperature of from 10° to 20° C. over a period of about one hour.

Next, the resulting reaction mixture was gradually heated to a reflux temperature and stirred for additional two hours or so at the reflux temperature. Thereafter, the reaction mixture was cooled to a temperature of from 0° to 5° C., and 20% by weight-aqueous sodium hydroxide solution was dropwise added cautiously.

Thereafter, an upper organic layer and a viscous lower layer were separated by decantation. Further, the lower layer was extracted with tetrahydrofuran, and the extract and the organic layer separated by decantation were combined. Thereafter, the organic layers were concentrated, to give a concentrate, which crystallized to give 15.26 g of white crystals.

The physical properties of the obtained crystals were as follows.

(1) Melting point: 81° to 83° C.

(2) IR (nujol mull) $\nu(cm^{-1})$: 3408, 3284, 3176, 1512, 1222, 1026.

(3) $^1$H-NMR (CDCl$_3$) δ (ppm): 7.15 (dd, 2H), 6.97 (dd, 2H), 3.35 (dd, 2H), 3.15 (dd, 2H), 2.36–2.71 (m, 6H), 1.55–1.86 (m, 3H).

It can be seen from the above results that the resulting crystals were consistent with (3S,4R)-trans-4-(4-fluorophenyl)-3-hydroxymethylpiperidine.

Example 10

(−)-(3S,4R)-4-(4-Fluorophenyl)-3-hydroxymethylpiperidine monohydrate

A 200-ml four-necked glass flask equipped with a thermometer and a reflux condenser was charged with 63 ml of toluene and 10.54 g (50.37 mmol) of (−)-(3S,4R)-4-(4-fluorophenyl)-3-hydroxymethylpiperidine, and the mixture was warmed and dissolved. 1.13 g (62.71 mmol) Of water was added to the above mixture at 50° C. to allow to crystallize. Thereafter, the mixture was kept for one hour at a temperature of from 20° to 30° C., and then the crystals were collected by filtration. The obtained crystals were thoroughly washed with 20 ml of toluene, to give white crystals of (−)-(3S,4R)-4-(4-fluorophenyl)-3-hydroxymethylpiperidine monohydrate. Thereafter, the crystals were dried under a reduced pressure at a temperature of 30° C. or lower, and weighed 10.24 g. The yield was 89.45% based on (−)-(3S,4R)-4-(4-fluorophenyl)-3-hydroxymethylpiperidine.

Example 11

The compound (3SR,4RS)-trans-4-(4-fluorophenyl)-3-hydroxymethylpiperidine was prepared by reducing (4RS,5SR)-trans-4-(4-fluorophenyl)-5-methoxycarbonylpiperidin-2-one with lithium aluminum hydride in the same manner as in Example 9. 9.0 g (43 mmol) Of the above (3SR,4RS)-trans-4-(4-fluorophenyl)-3-hydroxymethylpiperidine, 10.28 g (39.6 mmol) of (2R,3R)-o-chlorotartranilic acid, and 225 ml of water were mixed together. Thereafter, the resulting mixture was heated to dissolve the mixture at 78° C., and then the mixture was gradually cooled and then a small amount of seed crystals were added at 64° C. The mixture was further gradually cooled, and then the crystals were collected by filtration at 22° C. The resulting crystals were washed thrice with a 20-ml aliquot of water, and then the washed crystals were dried, to give 8.62 g of the crystals.

In order to further purify the resulting crystals, the crystals were recrystallized. Specifically, 100 ml of water was added to 8.62 g of the crystals prepared above, and then the temperature of the mixture was raised to 78° C., to dissolve the crystals. Thereafter, the mixture was gradually cooled, to allow crystals to precipitate at about 76° C. Further, the mixture was gradually cooled to a temperature of 20° C., and then the crystals were collected by filtration. The resulting crystals were washed thrice with a 10-ml aliquot of water, and then the washed crystals were dried, to give 7.25 g of crystals.

The physical properties of the obtained crystals were as follows.

(1) Melting point: 119° to 120° C.

(2) IR (nujol mull) $\nu(cm^{-1})$: 3336, 1608, 1524, 1512, 1486, 1440.

Next, 7.25 g of the crystals obtained above were decomposed with about 2%-aqueous sodium hydroxide solution, and the resulting mixture was extracted with ethyl acetate. Thereafter, the extract was concentrated to give 3.48 g of crystals.

The crystals were dissolved in a mixed solvent of an equivolume of ethyl acetate and toluene, and then a small amount of water was added thereto, to give 2.72 g of monohydrate crystals.

Next, the resulting crystals were analyzed by high performance liquid chromatography using a chiral HPLC column. The results showed that the optical purity was 100%. The crystals started melting at 79.5° C., and they melted at a temperature of 83° to 85° C.

The physical properties of the obtained crystals were as follows.

(1) $[\alpha]^{30}_D$: −35.7 (C=1%-methanol).

(2) IR (nujol mull) $\nu(cm^{-1})$: 3408, 3284, 1510, 1222, 1026.

(3) $^1$H-NMR (CDCl$_3$) δ (ppm): 7.17 (dd, 1H), 7.16 (dd, 1H), 6.99 (dd, 1H), 6.99 (t, 1H), 3.39 (dd, 1H), 3.35

(dd, 1H), 3.23 (dd, 1H), 3.15 (d br, 1H), 2.70 (dt, 1H), 2.57 (t, 1H), 2.45 (dt, 1H), 1.60–1.90 (m, 3H), 1.70 (s, 4H).

Example 12

A 200-ml four-necked glass flask equipped with a thermometer, a reflux condenser, and a dropping funnel was charged with 50 ml of anhydrous tetrahydrofuran and 1.51 g (39.8 mmol) of lithium aluminum hydride, and the slurry mixture was cooled to a temperature of 5° to 10° C.

To the above slurry, slurry prepared from 5.0 g (19.9 mmol) of (4RS,5SR)-trans-5-carboxy-4-(4-fluorophenyl)piperidin-2-one and 50 ml of tetrahydrofuran was dropwise added cautiously at a temperature of from 10° to 20° C. After the addition, the resulting mixture was stirred at a temperature of from 10° to 20° C. over a period of about one hour.

Then, the resulting reaction mixture was gradually heated to a reflux temperature, and kept at the reflux temperature for additional two hours or so. Thereafter, the reaction mixture was cooled to a temperature of from 0° to 5° C., and 20% by weight-aqueous sodium hydroxide solution was added dropwise thereto cautiously.

Thereafter, an upper organic layer and a viscous lower layer were separated by decantation. Further, the lower layer was extracted with tetrahydrofuran, and the extract and the organic layer were combined. Thereafter, the organic layer was concentrated, to give a concentrate, which crystallized to give 4.75 g of white crystals.

The physical properties of the obtained crystals were as follows.

(1) Melting point: 123° to 124° C.
(2) IR (nujol mull) ν(cm$^{-1}$): 3276, 3244, 3108, 1602, 1506, 1216, 1046, 834.
(3) $^1$H-NMR (CDCl$_3$) δ (ppm): 7.15 (dd, 2H), 6.97 (dd, 2H), 3.35 (dd, 2H), 3.15 (dd, 2H), 2.36–2.71 (m, 6H), 1.55–1.86 (m, 2H).

It can be seen from the above results that the resulting crystals were consistent with (3SR,4RS)-trans-4-(4-fluorophenyl)-3-hydroxymethylpiperidine.

Example 13

A 300-ml four-necked glass flask equipped with a thermometer, a reflux condenser, and a dropping funnel was charged with 100 ml of toluene, 116 ml of 5%-aqueous sodium bicarbonate solution, and 15.26 g of (3S,4R)-trans-4-(4-fluorophenyl)-3-hydroxymethylpiperidine. 11.83 g (69.34 mmol) Of benzyl chloroformate and 116 ml of 5%-aqueous sodium bicarbonate solution were added to the above mixture at a temperature of from 10 to 30° C. over a period of about 30 minutes.

The two-phase reaction mixture was stirred at a temperature of from 10° to 30° C. for about one hour. Thereafter, 35%-aqueous hydrochloric acid was added to the above mixture to make it acidic. The mixture was allowed to stand to separate into organic and aqueous layers, and the aqueous layer was removed therefrom. The obtained organic layer was washed with water and then dried over anhydrous magnesium sulfate. Thereafter, the dried organic layer was concentrated, to give 22.94 g of a slightly yellow, transparent oily product.

The physical properties of the resulting oily product were as follows.

(1) IR (neat) ν(cm$^{-1}$): 3448, 3032, 1686, 1606, 1512, 1472, 1442, 1222, 1126, 1014.

(2) $^1$H-NMR (CDCl$_3$) δ (ppm): 7.30–7.49 (m, 5H), 7.12 (dd, 2H), 6.98 (dd, 2H), 5.15 (s, 2H), 4.52 (dd, 1H), 4.28 (s br, 1H), 3.41 (dd, 1H), 3.23 (dd, 1H), 2.49–2.81 (m, 3H), 1.63–1.80 (m, 4H).

Example 14

A 200-ml four-necked glass flask equipped with a thermometer, a reflux condenser, and a dropping funnel was charged with 50 ml of toluene, 24 ml of 5%-aqueous sodium bicarbonate solution, and 3.0 g of (3SR,4RS)-trans-4-(4-fluorophenyl)-3-hydroxymethylpiperidine. 2.94 g (17.21 mmol) Of benzyl chloroformate and 29 ml of 5%-aqueous sodium bicarbonate were added to the above mixture at a temperature of from 10° to 30° C. over a period of about 30 minutes.

The two-phase reaction mixture was stirred at a temperature of from 10° to 30° C. for about one hour. Thereafter, 35%-aqueous hydrochloric acid was added to the above mixture to make it acidic. The mixture was allowed to stand to separate into organic and aqueous layers, and the aqueous layer was removed therefrom. The obtained organic layer was washed with water and then dried over anhydrous magnesium sulfate. Thereafter, the dried organic layer was concentrated, to give 4.92 g of slightly yellowish white crystals.

The physical properties of the resulting crystals were as follows.

(1) Melting point: 90° to 94° C.
(2) IR (neat) ν(cm$^{-1}$): 3452, 3032, 2920, 2864, 1690, 1604, 1512, 1472, 1278, 1226, 1126, 1064, 834.
(3) $^1$H-NMR (CDCl$_3$) δ (ppm): 7.30–7.49 (m, 5H), 7.12 (dd, 2H), 6.98 (dd, 2H), 5.15 (s, 2H), 4.52 (dd, 1H), 4.28 (s br, 1H), 3.41 (dd, 1H), 3.23 (dd, 1H), 2.49–2.81 (m, 3H), 1.63–1.80 (m, 4H).

From the above results, it was confirmed that the resulting crystals were consistent with (3SR,4RS)-trans-1-benzyloxycarbonyl-4-(4-fluorophenyl)-3-hydroxymethylpiperidine.

Example 15

A 300-ml four-necked glass flask equipped with a thermometer, a reflux condenser, and a dropping funnel was charged with 100 ml of toluene, 22.94 g of (3SR,4RS)-trans-1-benzyloxycarbonyl-4-(4-fluorophenyl)-3-hydroxymethylpiperidine, and 14.03 g (138.68 mmol) of triethylamine. 9.53 g (83.21 mmol) Of methanesulfonyl chloride was added dropwise to the above mixture at a temperature of from 10° to 30° C. over a period of about 30 minutes.

The reaction mixture was stirred at a temperature of from 10° to 30° C. for additional two hours. Thereafter, water was added to the resulting mixture, and the mixture was allowed to stand to separate into organic and aqueous layers, and the aqueous layer was removed therefrom. The obtained organic layer was washed with water and then dried over anhydrous magnesium sulfate. Thereafter, the dried organic layer was concentrated, to give 26.29 g of slightly yellow, transparent oily products.

The physical properties of the oily product, which solidified afterwards, were as follows.

(1) Melting point: 90° to 94° C.
(2) IR (neat) ν(cm$^{-1}$): 1696, 1512, 1472, 1436, 1358, 1224, 1176, 1130.
(3) $^1$H-NMR (CDCl$_3$) δ (ppm): 7.32–7.41 (m, 5H), 7.13 (dd, 2H), 7.02 (dd, 2H), 5.17 (s, 2H), 4.32–4.59 (m, 2H), 3.97 (dd, 1H), 3.81 (dd, 1H), 2.87 (s, 3H), 2.76–2.91 (m, 2H), 2.59 (m, 1H), 2.06 (m, 1H), 1.66–1.84 (m, 2H).

From the above results, it was confirmed that the resulting oily product was consistent with (3SR,4RS)-trans-1-benzyloxycarbonyl-4-(4-fluorophenyl)-3-methylsulfonyloxymethylpiperidine.

Example 16

A 200-ml four-necked glass flask equipped with a thermometer, a reflux condenser, and a dropping funnel was charged with 50 ml of toluene, 4.92 g of (3SR,4RS)-trans-1-benzyloxycarbonyl-4-(4-fluorophenyl)-3-hydroxymethylpiperidine, and 1.75 g (21.51 mmol) of pyridine. 1.84 g (16.06 mmol) Of methanesulfonyl chloride was added dropwise to the above mixture at a temperature of from 10° to 30° C. over a period of about 30 minutes.

The reaction mixture was stirred at a temperature of from 10° to 30° C. for additional two hours. Thereafter, water was added to the resulting mixture, and the mixture was allowed to stand to separate into organic and aqueous layers, and the aqueous layer was removed therefrom. The obtained organic layer was washed with water and then dried over anhydrous magnesium sulfate. Thereafter, the dried organic layer was concentrated, to give 6.57 g of a slightly yellow, transparent oily product.

The physical properties of the obtained oily product were as follows.

(1) IR (neat) ν(cm$^{-1}$): 3028, 2936, 1694, 1512, 1470, 1436, 1358, 1278, 1228, 1176, 1130, 960, 834.

(2) $^1$H-NMR (CDCl3) δ (ppm): 7.32–7.41 (m, 5H), 7.13 (dd, 2H), 7.02 (dd, 2H), 5.17 (s, 2H), 4.32–4.59 (m, 2H), 3.97 (dd, 1H), 3.81 (dd, 1H), 2.87 (s, 3H), 2.76–2.91 (m, 2H), 2.59 (m, 1H), 2.06 (m, 1H), 1.66–1.84 (m, 2H).

From the above results, it was confirmed that the resulting oily product was consistent with (3SR,4RS)-trans-1-benzyloxycarbonyl-4-(4-fluorophenyl)-3-methylsulfonyloxymethylpiperidine.

Example 17

A 300-ml four-necked glass flask equipped with a thermometer and a reflux condenser was charged with 200 ml of methanol, 25.85 g of 3,4-methylenedioxyphenol, 26.29 g of (3S,4R)-trans-1-benzyloxycarbonyl-4-(4-fluorophenyl)-3-methylsulfonyloxymethylpiperidine, and 34.90 g of 28% by weight sodium methylate. The mixture was stirred and then heated to a reflux temperature.

The resulting reaction mixture was refluxed for about 16 hours, and then methanol was distilled off. The remaining product was poured into a liquid mixture of 200 ml of toluene and 200 ml of iced water. Thereafter, the toluene layer was separated therefrom, and the aqueous layer was further extracted with toluene.

Then, the toluene layer which was firstly separated was combined with the toluene layer obtained by re-extraction, to give a toluene solution. The toluene solution was washed with 5%-aqueous sodium hydroxide solution, and then with water. The washed toluene solution was dried over anhydrous magnesium sulfate, and the resulting solution was concentrated, to give 25.57 g of a brown oily product.

The physical properties of the obtained oily product were as follows.

(1) IR (neat) ν(cm$^{-1}$): 1704, 1690, 1510, 1502, 1486, 1470, 1276, 1222, 1184, 1130, 1038.

(2) $^1$H-NMR (CDCl$_3$) δ (ppm): 7.34–7.39 (m, 5H), 7.11 (dd, 2H), 6.97 (dd, 2H), 6.61 (d, 1H), 6.34 (d, 1H), 6.12 (dd, 1H), 5.87 (s, 2H), 5.17 (s, 2H), 4.02–4.53 (m, 2H), 3.59 (dd, 1H), 3.44 (dd, 1H), 2.71–3.15 (m, 3H), 1.74–2.02 (m, 3H).

From the above results, it was confirmed that the resulting oily product was consistent with (3S,4R)-trans-1-benzyloxycarbonyl-4-(4-fluorophenyl)-3-[(3,4-methylenedioxyphenyl)oxymethyl]piperidine.

Example 18

A 200-ml four-necked glass flask equipped with a thermometer and a reflux condenser was charged with 100 ml of methanol, 4.30 g of 3,4-methylenedioxyphenol, 6.57 g of (3SR,4RS)-trans-1-benzyloxycarbonyl-4-(4-fluorophenyl)-3-methylsulfonyloxymethylpiperidine, and 6.42 g of 28% by weight sodium methylate. The mixture was stirred and then heated to a reflux temperature.

The resulting reaction mixture was refluxed for about 16 hours, and then methanol was distilled off. The remaining product was poured into a liquid mixture of 100 ml of toluene and 100 ml of iced water. Thereafter, the toluene layer was separated therefrom, and the aqueous layer was further extracted with toluene.

Then, the toluene layer which was firstly separated was combined with the toluene layer obtained by re-extraction, to give a toluene solution. The toluene solution was washed with 5% aqueous sodium hydroxide solution, and then with water. The washed toluene solution was dried over anhydrous magnesium sulfate, and the resulting solution was concentrated, to give 7.23 g of brown crystals.

The physical properties of the resulting crystals were as follows.

(1) Melting point: 127° to 128° C.

(2) IR (nujol mull) ν(cm$^{-1}$): 1688, 1504, 1278, 1224, 1192, 1122, 1040, 830.

(3) $^1$H-NMR (CDCl$_3$) δ (ppm): 7.34–7.39 (m, 5H), 7.11 (dd, 2H), 6.97 (dd, 2H), 6.61 (d, 1H), 6.34 (d, 1H), 6.12 (dd, 1H), 5.87 (s, 2H), 5.17 (s, 2H), 4.02–4.53 (m, 2H), 3.59 (dd, 1H), 3.44 (dd, 1H), 2.71–3.15 (m, 3H), 1.74–2.02 (m, 3H).

From the above results, it was confirmed that the resulting crystals were consistent with (3SR,4RS)-trans-1-benzyloxycarbonyl-4-(4-fluorophenyl)-3-[(3,4-methylenedioxyphenyl)oxymethyl]piperidine.

Example 19

A 500-ml autoclave was charged with 200 ml of methanol, 25.57 g (55.2 mmol) of (3S,4R)-trans-1-benzyloxycarbonyl-4-(4-fluorophenyl)-3-[(3,4-methylenedioxyphenyl)oxymethyl]piperidine, 2.80 g of palladium carbon (catalyst), and then hydrogen gas was supplied to the autoclave under the conditions of pressure 3 to 5 kgf/cm$^2$ and reaction temperature 40° to 50° C. Thereafter, the resulting mixture was stirred for two hours under the same conditions as given above, and then the obtained mixture was cooled to a temperature of from 20° to 30° C. Subsequently, after adjusting the pressure to a normal pressure, the reaction mixture was filtered to remove the catalyst, and then the filtrate was concentrated by removing methanol using a rotary evaporator under a reduced pressure, to give 17.94 g of a brown oily product (3S,4R)-trans-4-(4-fluorophenyl)-3-[(3,4-methylenedioxyphenyl) oxymethyl]piperidine.

The yield of the oily product was 98.7% based on (3S,4R)-trans-1-benzyloxycarbonyl-4-(4-fluorophenyl)-3-[(3,4-methylenedioxyphenyl)oxymethyl]-piperidine.

Example 20

A 300-ml four-necked glass flask equipped with a thermometer and a gas inlet tube was charged with 17.94 g of (3S,4R)-trans-4-(4-fluorophenyl)-3-[(3,4-methylenedioxyphenyl)oxymethyl]piperidine and 200 ml of anhydrous isopropanol under nitrogen gas atmosphere, and then the mixture was cooled to a temperature of 0° to 5° C. Thereafter, dry hydrogen chloride gas was introduced to the reaction mixture through a gas inlet tube at a temperature of 0° to 5° C. over a period of 45 minutes to allow the crystals to precipitate.

The formed crystals were collected by filtration, and washed with 20 ml of anhydrous isopropanol. Thereafter, the washed crystals were thoroughly dried under a reduced pressure, to give 12.73 g of white crystals of anhydrous (3S,4R)-trans-4-(4-fluorophenyl)-3-[(3,4-methylenedioxyphenyl)oxymethyl]piperidine hydrochloride. The yield of the resulting white crystals was 63.9% based on (3S,4R)-trans-4-(4-fluorophenyl)-3-[(3,4-methylenedioxyphenyl)oxymethyl]piperidine.

The physical properties of the resulting crystals were given below, which were consistent with the literature values, so that the resulting crystals were confirmed to be anhydrous (3S,4R)-trans-4-(4-fluorophenyl)-3-[(3,4-methylenedioxyphenyl)oxymethyl]-piperidine hydrochloride.

(1) Melting point: 116.4° to 118.4° C.
(2) IR (nujol mull) $\nu$(cm$^{-1}$): 3628, 3420, 1514, 1494, 1220, 1194, 1034, 886, 840.
(3) $^1$H-NMR (CDCl$_3$) $\delta$ (ppm): 9.86 (s br, 2H), 7.21 (dd, 2H), 6.99 (dd, 2H), 6.62 (d, 1H), 6.32 (d, 1H), 6.11 (dd, 1H), 5.88 (s, 2H), 3.71 (m, 2H), 3.60 (dd, 1H), 3.48 (dd, 1H), 2.86–3.21 (m, 3H), 2.66–2.96 (m, 1H), 2.39 (ddd, 1H), 2.03 (d br, 1H).

Example 21

Preparation of (3S,4R)-1-tert-butoxycarbonyl-4-(4-fluorophenyl)-3-hydroxymethylpiperidine A 500-ml four-necked glass flask equipped with a thermometer was charged with 127.2 ml of toluene and 25.43 g (111.89 mmol) of (−)-(3S,4R)-4-(4-fluorophenyl)-3-hydroxymethylpiperidine monohydrate, and the mixture was homogeneously stirred at a temperature of from 20° to 30° C. Thereafter, while stirring, 24.42 g (111.89 mmol) of di-tert-butyl dicarbonate was added dropwise to the mixture at a temperature of from 20° to 30° C. Subsequently, the reaction mixture was stirred for 30 minutes at a temperature of from 20° to 30° C., and then the solvent was removed under a reduced pressure using a rotary evaporator, to give a concentrate containing a crude oil product of (3S,4R)-1-tert-butoxycarbonyl-4-(4-fluorophenyl)-3-hydroxymethylpiperidine. The yield was 102.61% based on (−)-(3S,4R)-4-(4-fluorophenyl)-3-hydroxymethylpiperidine.

Example 22

Preparation of (3S,4R)-1-tert-butoxycarbonyl-4-(4-fluorophenyl)-3-hydroxymethylpiperidine A 500-ml four-necked glass flask equipped with a thermometer was charged with 113.9 ml of toluene, 48.69 g (100 mmol) of (3S,4R)-4-(4-fluorophenyl)-3-hydroxymethylpiperidine o-chloro-L-tartranic acid monohydrate, 91.9 ml of water and 22.92 g (105 mmol) of di-tert-butyl dicarbonate, and then the mixture was stirred at a temprature of from 20° to 30° C. Thereafter, while stirring, 17.6 g (110 mmol) of 25% aqueous sodium hydroxide solution was added dropwise to the mixture at a temperature of 20° to 50° C. The reaction solution was heated to a temperature of 45° to 55° C. and stirred at the same temperature for 30 minutes, and then the aqueous layer was removed therefrom. Further, 34.1 g of water was added to the organic layer, and the organic layer was washed with water, and then the aqueous layer was removed therefrom. The organic layer was concentrated by removing the solvent using a rotary evaporator under a reduced pressure, to give a concentrate containing a crude oil product of (3S,4R)-1-tert-butoxycarbonyl-4-(4-fluorophenyl)-3-hydroxymethylpiperidine in the amount of 32.14 g. The yield was 103.89% based on (3S,4R)-4-(4-fluorophenyl)-3-hydroxymethylpiperidine o-chloro-L-tartranic acid monohydrate.

Example 23

Preparation of (3S,4R)-1-tert-butoxycarbonyl-4-(4-fluorophenyl)-3-methylsulfonyloxymethylpiperidine A 500-ml four-necked glass flask equipped with a thermometer was charged with 153.5 ml of toluene and 23.61 g (76.31 mmol) of (3S,4R)-1-tert-butoxycarbonyl-4-(4-fluorophenyl)-3-hydroxymethylpiperidine, and 8.49 g (83.90 mmol) of triethylamine was added to the above mixture, and then the mixture was stirred at a temperature of from 10° to 30° C. Thereafter, while stirring, 8.74 g (76.30 mmol) of methanesulfonyl chloride was added dropwise to the mixture at a temperature of from 10° to 20° C. Thereafter, the reaction mixture was stirred for additional four hours at a temperature of 20° to 30° C., and 85.7 ml of water was added to the resulting reaction mixture, and then the aqueous layer was removed therefrom. Further, the organic layer was washed with brine by adding 85.7 ml of water and 4.3 g of sodium chloride, and then separated to remove the aqueous layer therefrom. Thereafter, the organic layer was concentrated by removing the solvent under a reduced pressure using a rotary evaporator, to give a concentrate containing a crude oil product of (3S,4R)-1-tert-butoxycarbonyl-4-(4-fluorophenyl)-3-methylsulfonyloxymethylpiperidine. The yield was 98.62% based on (3S,4R)-1-tert-butoxycarbonyl-4-(4-fluorophenyl)-3-hydroxymethylpiperidine.

Example 24

Preparation of (3S,4R)-1-tert-butoxycarbonyl-4-(4-fluorophenyl)-3-[(3,4-methylenedioxyphenyl)-oxymethyl]piperidine A 500-ml four-necked glass flask equipped with a thermometer and a reflux condenser was charged with 19.44 g (50.17 mmol) of (3S,4R)-1-tert-butoxycarbonyl-4-(4-fluorophenyl)-3-methylsulfonyloxymethylpiperidine, 117 ml of toluene, 8.32 g (60.24 mmol) of sesamol, and 10.65 g (55.20 mmol) of a 28%-sodium methylate methanol solution, while stirring, under nitrogen gas atmosphere. Thereafter, the resulting mixture was heated to a reflux temperature, and kept at the above reflux temperature for additional 6 to 18 hours, and cooled. Then, the reaction mixture was sufficiently washed with an alkaline aqueous solution by adding 117 ml of water, 5.85 g of sodium chloride, and 2.0 g of 99%-flaky sodium hydroxide to the resulting mixture, and then the aqueous layer was removed. Thereafter, the organic layer was concentrated under a reduced pressure using a rotary evaporator, to give a concentrate containing a crude oil product of (3S,4R)-1-tert-butoxycarbonyl-4-(4-fluorophenyl)-3-[(3,4-methylenedioxyphenyl)oxymethyl]piperidine.

The yield was 98.06% based on (3S,4R)-1-tert-butoxycarbonyl-4-(4-fluorophenyl)-3-methylsulfonyloxymethylpiperidine.

The physical properties of the resulting compound were as follows.

(1) IR (paste) v(cm$^{-1}$): 1682, 1510, 1488, 1216, 1184.
(2) $^1$H-NMR (CDCl$_3$) δ (ppm): 7.12 (m, 2H), 6.97 (m, 2H), 6.62 (d, 1H), 6.34 (d, 1H), 6.13 (dd, 1H), 5.87 (s, 2H), 3.60 (dd, 1H), 3.44 (dd, 1H), 2.63–2.88 (m, 3H), 2.01 (m, 1H), 1.72 (m, 1H), 1.50 (s, 9H).

Example 25

Preparation of (–)-(3S,4R)-4-(4-fluorophenyl)-3-[(3,4-methylenedioxyphenyl)-oxymethyl]piperidine hydrochloride A 100 ml four-necked glass flask equipped with a thermometer and a reflux condenser was charged with 75.7 ml of isopropanol and 9.15 g (21.30 mmol) of (3S,4R)-1-tert-butoxycarbonyl-4-(4-fluorophenyl)-3-[3,4-methylenedioxyphenyl)oxymethyl]piperidine, and the mixture was dissolved therein under nitrogen gas atmosphere. Thereafter, 9.70 g (53.21 mmol calculated as hydrochloric acid) of a 20%-isopropanol solution of hydrochloric acid was added dropwise to the above reaction mixture at a temperature of from 20° to 30° C., and stirred at a temperature of from 20° to 30° C. for one hour. Subsequently, the resulting mixture was heated to a reflux temperature. After stirring the reaction mixture at the above reflux temperature for additional two hours, the reaction mixture was cooled, and then a small amount of seed crystals of (–)-(3S,4R)-4-(4-fluorophenyl)-3-[(3,4-methylenedioxyphenyl)oxymethyl]piperidine hydrochloride containing isopropanol was added thereto, to afford a crystalline product. After sufficient crystallization, the reaction mixture was cooled to a temperature of from 0° to 5° C., and then the cooled mixture was kept at a temperature of from 0° to 5° C. for one hour. The resulting crystals were collected by filtration, and the crystals were sufficiently washed with isopropanol, to give white crystals, which were (–)-(3S,4R)-4-(4-fluorophenyl)-3-[(3,4-methylenedioxyphenyl)oxymethyl]piperidine hydrochloride. The resulting crystals were dried under a reduced pressure at 90° C., to give 6.17 g of a product.

The yield was 79.17% based on (3S,4R)-1-tert-butoxycarbonyl-4-(4-fluorophenyl)-3-[(3,4-methylenedioxyphenyl)oxymethyl]piperidine.

The above crystals contained isopropanol in an amount of 2.51% by weight.

Experimental Example

A four-necked glass flask was charged with 223.2 g (0.6777 mol) of (3S,4R)-4-(4-fluorophenyl)-3-[(3,4-methylenedioxyphenyl)oxymethyl]piperidine and 2150 ml of isopropanol, and 135.9 g (0.7454 mol) of a 20% isopropanol solution of HCl was added dropwise to the above mixture over a period of 10 minutes at a temperature of from 50° to 60° C.

Next, 11.21 g of activated carbon was added to the mixture to decolorize and the mixture was stirred over a period of 15 minutes at a temperature of from 60° to 70° C. Thereafter, the resulting mixture was filtered to remove the activated carbon, and then washed with 225 ml of hot isopropanol of a temperature of from 70° to 80° C. As a result, the solution could be substantially decolorized.

The filtrate was cooled to a temperature of from 45° to 50° C., and then seed crystals were added thereto, to allow crystals to precipitate. Thereafter, the slurry of crystals was kept for one hour at a temperature of from 0° to 5° C. Subsequently, the crystals were collected by filtration, and then the obtained crystals were washed with 640 ml of cold isopropanol of a temperature of from about 0° to about 5° C. The washed crystals were dried under a reduced pressure at 70° C., to give 209.4 g (0.5117 mol) of white paroxetine hydrochloride containing 10.6% of isopropanol.

Further, 180.3 g (0.4406 mol) of the paroxetine hydrochloride was dried under a reduced pressure, to give 157.7 g (0.4216 mol) of white paroxetine hydrochloride containing 2.2% of isopropanol.

With the paroxetine hydrochloride containing 10.6% of isopropanol, the profile between the drying temperature and the residual amount of isopropanol was examined. The results are shown in Table 1.

TABLE 1

| Drying Period (Hr.) | Residual Amount of Isopropanol (% by weight) | | | | |
|---|---|---|---|---|---|
| | Drying Temp. (70° C.) | Drying Temp. (80° C.) | Drying Temp. (90° C.) | Drying Temp. (100° C.) | Drying Temp. (110° C.) |
| 0 | | (10.58) | (10.58) | (10.58) | (10.58) |
| 3 | 10.58 | | | | |
| 8 | | | | | 0.24 |
| 10 | 9.96 | | | | |
| 12 | | 8.72 | | 0.50 | 0.20 |
| 14 | | | 4.25 | | |
| 24 | | 6.80 | | 0.39 | 0.13 |
| 26 | | | 2.34 | | |
| 32 | | | 2.20 | | |
| 48 | | 4.44 | | | |
| 72 | 9.90 | 4.09 | | | |
| 96 | | 3.73 | | | |
| 168 | | 2.44 | | | |

It can be seen from Table 1 that by the combinations of the drying temperatures ranging from 80° to 110° C. and the drying time course of 168 hours, the residual amount of isopropanol can be controlled within a range of from 0.1 to 5%.

As explained above, according to the present invention, a compound highly useful as an intermediate for the preparation of paroxetine can be advantageously prepared in a simple manner.

Also, paroxetine hydrochlorides and anhydrous crystals can be prepared in a simple manner from the above compound.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for preparing a crystalline hydrochloride of (3S, 4R)-trans-4-(4-fluorophenyl)-3-[(3,4-methylenedioxyphenyl)oxymethyl]piperidine containing isopropanol, comprising the steps of:

(A) reacting 4-fluorobenzaldehyde with acetic acid ester represented by the formula:

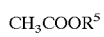

wherein R$^5$ is an alkyl group having 1 to 4 carbon atoms to give a 4-fluorocinnamic acid ester, (B) reacting the resulting 4-fluorocinnamic acid ester with a cyanoacetic acid ester represented by the formula:

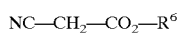

wherein R⁶ is an alkyl group having 1 to 4 carbon atoms to give a glutaric acid ester compound represented by the formula (X):

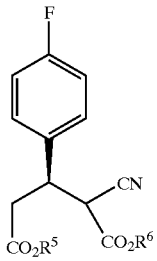

(X)

wherein R⁵ and R⁶ are as defined above, (C) reducing the resulting glutaric acid ester compound to give (±)-cis, trans-4-(4-fluorophenyl)-5-alkoxycarbonyl-piperidine-2-one represented by the formula (IX):

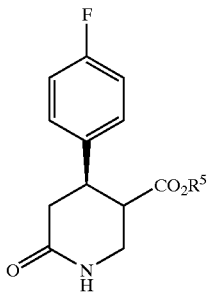

(IX)

wherein R⁵ is as defined above, (D) transforming the (±)-cis, trans-4-(4-fluorophenyl)-5-alkoxycarbonylpiperidine-2-one represented by the formula (IX) in the presence of a base to give (4RS, 5SR)-trans-4-(4-fluorophenyl)-5-alkoxycarbonylpiperidine-2-one;

reducing the (4RS, 5SR)-trans-4-(4-fluorophenyl)-5-alkoxycarbonylpiperidine-2-one with a metal hydride compound to give (3SR, 4RS)-trans-4-(4-fluorophenyl)-3-hydroxymethyl piperidine, and optically resolving the (3SR, 4RS)-trans-4-(4-fluorophenyl)-3-hydroxymethylpiperidine to give (3S, 4R)-trans-4-(4-fluorophenyl)-3-hydroxymethylpiperidine represented by the formula (II):

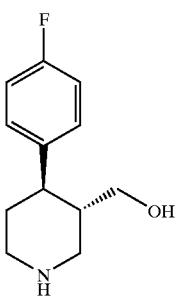

(II)

(E) reacting the (3S, 4R)-trans-4-(4-fluorophenyl)-3-hydroxymethylpiperidine represented by the formula (II) with a protecting agent represented by the formula (III):

(III)

wherein R³ is a tert-butyl group, and Y is a tert-butoxycarbonyloxy group, to give a carbamate compound represented by the formula (IV):

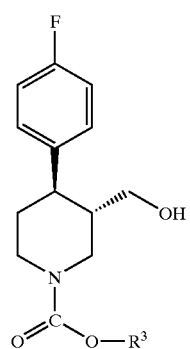

(IV)

wherein R³ is as defined above, (F) reacting said carbamate compound with sulfonic acid chloride represented by the formula (V):

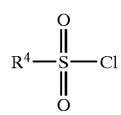

(V)

wherein R⁴ is an alkyl group having 1 to 2 carbon atoms or a phenyl group which may have a methyl group at the 4-position, to give a sulfonic acid ester represented by the formula (VI):

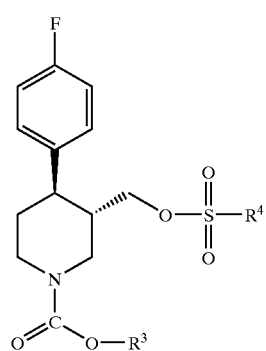

(VI)

wherein R³ and R⁴ are as defined above;

(G) reacting said sulfonic acid ester with 3,4-methylenedioxyphenol under basic conditions, to give a piperidine compound represented by the formula (VII):

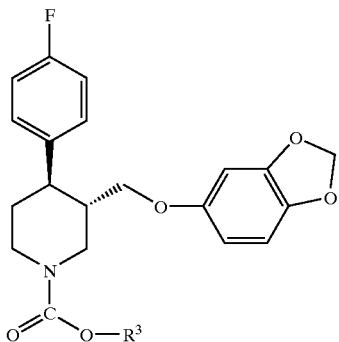

(VII)

wherein R³ is as defined above; and (H) treating said piperidine compound with hydrogen chloride in isopropanol.

2. The method according to claim 1, wherein the reducing step of (C) is carried out by catalytic hydrogenation.

3. The method according to claim 1, wherein the optical resolving in the step (D) is carried out with (2R, 3R)-o-chlorotartranilic acid.

4. The method according to claim 1, wherein said sulfonic acid chloride is methanesulfonyl chloride.

* * * * *